United States Patent [19]
Nakashima et al.

[11] Patent Number: 5,837,687
[45] Date of Patent: Nov. 17, 1998

[54] AZAPEPTIDE DERIVATIVE

[75] Inventors: Yoshiharu Nakashima; Michiyo Hizuka; Yasushi Higashide; Tetsuaki Yamaura; Hiroshi Ikawa, all of Tokyo, Japan

[73] Assignee: Fujirebio Inc., Tokyo, Japan

[21] Appl. No.: 406,053

[22] Filed: Mar. 17, 1995

[30] Foreign Application Priority Data

Mar. 17, 1994 [JP] Japan ..................................... 6-047206
Apr. 19, 1994 [JP] Japan ..................................... 6-080547

[51] Int. Cl.$^6$ .............................. A61K 38/07; C07K 5/04
[52] U.S. Cl. .............................. 514/18; 514/19; 530/330; 530/331
[58] Field of Search .................. 514/18, 19, 17; 50/330, 331

[56] References Cited

U.S. PATENT DOCUMENTS

| | | | |
|---|---|---|---|
| 4,421,744 | 12/1983 | Gormley | 514/17 |
| 5,128,447 | 7/1992 | Rovero et al. | 530/328 |
| 5,164,372 | 11/1992 | Matsuo et al. | 514/19 |
| 5,304,632 | 4/1994 | Vaudry et al. | 530/327 |
| 5,410,019 | 4/1995 | Coy et al. | 530/323 |
| 5,420,297 | 5/1995 | Matsuo et al. | 548/525 |
| 5,468,731 | 11/1995 | Matsuo et al. | 514/18 |
| 5,602,231 | 2/1997 | Cotton et al. | 530/334 |
| 5,654,400 | 8/1997 | Matsuo et al. | 530/345 |

FOREIGN PATENT DOCUMENTS 0076557   4/1983   European Pat. Off. .

OTHER PUBLICATIONS

Chemical Abstracts, vol. 59, No. 10, Nov. 11, 1963. 11324e to 11325a.
Chemical Abstracts, vol. 64, No. 4, Feb. 14, 1966. 6750e to 6753a.

*Primary Examiner*—Robert H. Harrison
*Attorney, Agent, or Firm*—Oblon, Spivak, McClelland, Maier & Neustadt, P.C.

[57] ABSTRACT

Disclosed is an azapeptide derivative represented by the formula (I):

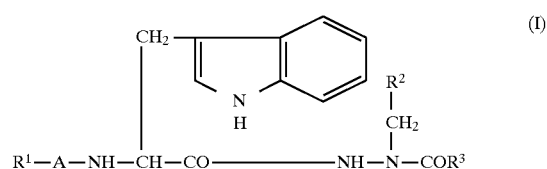

wherein A represents a direct bond, an α-amino acid or a residue of a dipeptide; $R^1$ represents a hydrogen atom or a protective group for a terminal amino group;

$R^2$ represents a phenyl group or a phenyl group substituted by one or two substituents selected from the group consisting of a lower alkyl group, halogen atom, hydroxyl group which may be protected, nitro group, amino group which may be protected and perhalo lower alkyl group; and $R^3$ represents a hydroxyl group or a protective group for a terminal carboxyl group, and a salt thereof, and an agent for curing nervous inflammation of respiratory apparatus, asthma and bronchospasm comprising the azapeptide derivative represented by the formula (I) or a salt thereof as an active ingredient.

17 Claims, No Drawings

AZAPEPTIDE DERIVATIVE

BACKGROUND OF THE INVENTION

This invention relates to a novel azapeptide derivative which is an antagonist of a receptor of neurokinin A (NKA) which is a tachykinin neuropeptide, and a salt thereof.

As transmitters of primary sensory nerves, there has been known the tachykinin family in which peptides have the C-terminal sequence (-Phe-X-Gly-Leu-Met-$NH_2$). As said neuro-peptides derived from mammals, there have been known neurokinin A (NKA), substance P (SP) and neurokinin B (NKB) shown below (Kimura, S., et al., Proc. Japan Acd., 59B, pp. 101 to 104 (1983)).

NKA: His-Lys-Thr-Asp-Ser-Phe-Val-Gly-Leu-Met-$NH_2$
NKB: Asp-Met-His-Asp-Phe-Phe-Val-Gly-Leu-Met-$NH_2$
SP: Arg-Pro-Lys-Prc-Gln-Gln-Phe-Phe-Gly-Leu-Met-$NH_2$

These peptides exhibit excitation activities in central and peripheral nervous systems and exhibit analogous physiological activities such as constriction of smooth muscle (other than blood vessels), vasodilation, stimulation of endocrine and exocrine glands, exudation of plasma and immunity-inflammation in non-nervous tissues (Perow, B., Pharmacol. Rev., 35, p. 86 (1983), Yukio Takano, Taiyu Kamiya, Yakugaku Zasshi 108, p. 201 (1988), Maggio, J. M., Ann. Rev. Neurosci. 11, p. 13 (1989)).

It has been known that among them, NKA coexists with SP to exhibit potent activities of inducing contraction of respiratory smooth muscle in asthma, sthenia of secretion of respiratory mucosa and edema of respiratory mucosa (Lundberg, J. M., Arch. Int. Pharmacodyn. 303, p. 9 (1990), Barnes, P. J., Arch. Int. Pharmacodyn. 303, p. 67 (1990)). Also, NKA has been known as a substance having a potent constriction activity even in tissues other than respiratory tracts, for example, bladder, stomach and intestines. Thus, an antagonist of NKA has a possibility as an agent for curing bronchial asthma, gastrointestinal hyperkinesis and incontinence of urine.

As a compound having a NKA antagonistic activity, there have been reported peptide derivatives having 6 or more amino acid residues, such as peptide I: [$Tyr^5$, D-$Trp^{6,8,9}$, $Arg^{10}$]NKA(4–10)
peptide II: [$Tyr^5$, D-$Trp^{6,8,9}$, $Arg^{10}$]NKA(3–10)
peptide III: Ac-Leu-Asp-Gln-Trp-Phe-Gly-$NH_2$ (Br. J. Pharmacol., 100, pp. 588 to 592 (1990), Japanese Provisional Patent Publication No. 17098/1991).

In general, it is estimated that a long chain peptide derivative is susceptible to enzymatic degradation and has poor absorption property and transition property in tissues. Thus, as compound which is more useful as a medicine, a compound having a low molecular weight and a compound having enzyme resistance have been demanded.

SUMMARY OF THE INVENTION

An object of the present invention is to provide a novel azapeptide derivative having a potent NKA antagonistic activity which is an effective and sustained activity in vivo.

In order to achieve the above object, the present inventors have found that an azapeptide derivative represented by the formula (I) shown below, comprising azaamino acid in which a carbon atom at α-position of phenylalanine or tyrosine is replaced with a nitrogen atom exhibit a potent NKA antagonistic activity which is an effective and sustained activity in vivo, to accomplish the present invention.

That is, the present invention is an azapeptide derivative represented by the formula (I):

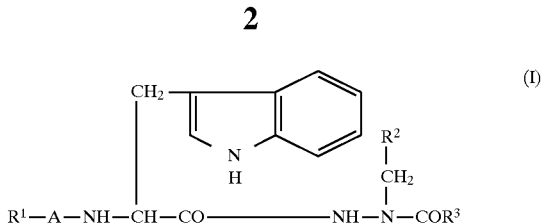

wherein A represents a direct bond, an α-amino acid or a residue of a dipeptide; $R^1$ represents a hydrogen atom or a protective group for a terminal amino group;

$R^2$ represents a phenyl group or a phenyl group substituted by one or two substituents selected from the group consisting of a lower alkyl group, halogen atom, hydroxyl group which may be protected, nitro group, amino group which may be protected and perhalo lower alkyl group; and $R^3$ represents a hydroxyl group or a protective group for a terminal carboxyl group, and a salt thereof.

DESCRIPTION OF THE PREFERRED EMBODIMENTS

In the following, the present invention is explained in detail.

In the above formula (I), the α-amino acid of A includes a natural α-amino acid and a non-natural α-amino acid. Also, the α-amino acid includes a L-isomer, a D-isomer and a DL-racemic compound.

As the natural α-amino acid, there may be mentioned glycine, alanine, valine, leucine, isoleucine, serine, methionine, threonine, phenylalanine, tyrosine, tryptophan, cysteine, cystine, proline, 4-hydroxyproline, histidine, aspartic acid, asparagine, glutamic acid, glutamine arginine, citrulline, ornithine and lysine.

As the non-natural α-amino acid, there may be mentioned norleucine, norvaline, alloisoleucine, homoarginine, thiaproline, methionine sulfoxide, methionine sulfone, dehydroproline, homoserine, cyclohexylglycine (Chg), α-amino-n-butyric acid (Aba), cyclohexylalanine (Cha), aminophenylbutyric acid (Pba), phenylalanines in which a phenyl portion of phenylalanine is substituted by 1 or 2 of a lower alkyl, a lower alkoxy, a halogen or a nitro group, or substituted by a methylenedioxy group, β-(2- or 3-thienyl) alanine, β-(2- or 3-furanyl)alanine, β-(2-, 3- or 4-pyridyl) alanine, β-(benzothiophen-2- or 3-yl)alanine and β-(1- or 2-naphthyl)alanine.

Preferred is a natural α-amino acid, and particularly preferred is methionine, aspartic acid, asparagine, glutamic acid, glutamine, arginine, citrulline or ornithine; as the non-natural α-amino acid, methionine sulfoxide is particularly preferred; and as the dipeptide, a dipeptide of the above α-amino acid is preferred, and aspartic acid-glutamine and asparagine-glutamine are particularly preferred.

The α-amino acid and the dipeptide of A includes those having a substituent shown below at a side chain thereof.

a) As a substituent of an amino group, there may be mentioned, for example, a substituted or unsubstituted lower alkanoyl group such as formyl, acetyl, propionyl and trifluoroacetyl; a phthaloyl group; a lower alkoxycarbonyl group such as t-butoxycarbonyl and t-amyloxycarbonyl; a substituted or unsubstituted aralkoxycarbonyl group such as benzyloxycarbonyl and 4-nitrobenzyloxycarbonyl; a substituted or unsubstituted allenesulfonyl group such as benzenesulfonyl and tosyl; a 2-nitrophenylsulfenyl group; and an aralkyl group such as trityl and benzyl. As a substituent of a guanidino group, there may be mentioned, for example, nitro, benzyloxycarbonyl, tosyl, 4-methoxybenzenesulfonyl and 4-methoxy-2,3,6-trimethylbenzenesulfonyl.

b) As an amidated carboxyl group, there may be mentioned, for example, a carboxyl group substituted by a lower alkyl-substituted amide which is obtained by being substituted by one or two substituted or unsubstituted lower alkyl group(s) such as methyl, ethyl, isobutyl, 2-hydroxyethyl, 2-methoxyethyl and 2-benzyloxyethyl; an aryl-substituted amide obtained by being substituted by phenyl or the like; an aralkyl-substituted amide obtained by being substituted by a substituted or unsubstituted aralkyl group such as benzyl, 4-fluorobenzyl, phenethyl, 2,4-dimethoxybenzyl, benzhydryl, 4,4'-dimethoxybenzhydryl and xanthyl; and a heterocyclic imide obtained by being substituted by morpholino, thiomorpholino, pyrrolidine-1-yl, pyrazolidin-1-yl, piperazino or pyrrolin-1-yl.

c) As an esterified carboxyl group, there may be mentioned, for example, a carboxyl group esterified by a substituted or unsubstituted lower alkyl group such as methyl, ethyl, trichloroethyl and t-butyl; a cycloalkyl group such as cyclopentyl and cyclohexyl; and a substituted or unsubstituted aralkyl group such as benzyl, phenacyl, 4-nitrobenzyl, 4-methoxybenzyl and benzhydryl.

d) As a substituent of a thiol group, there may be mentioned, for example, a substituted or unsubstituted lower alkyl group such as methyl, ethyl, t-butyl and acetoamidomethyl; and a substituted or unsubstituted aralkyl group such as benzyl, trityl and 4-methoxybenzyl.

e) As a substituent of a hydroxyl group, there may be mentioned, for example, a lower alkyl group such as t-butyl; a cycloalkyl group such as cyclohexyl; a substituted or unsubstituted aralkyl group such as benzyl, 2-nitrobenzyl and 3-bromobenzyl; an acyl group such as acetyl and benzoyl; t-butyloxycarbonyl; and benzyloxycarbonyl.

A particularly preferred A may include a direct bond, methionine, methioninesulfone, arginine, aspartic acid, asparagine, glutamine, citrulline, ornithine, aspartic acid β-benzyl ester (Asp(OBzl)), $N^{\omega}$-nitro-arginine (Arg(NO$_2$)), aspartic acid-glutamine or asparagine-glutamine.

As a protective group for the terminal amino group of $R^1$, there may be mentioned an acyl group, an alkoxycarbonyl group having 1 to 6 alkoxy carbon atoms, an aralkyloxycarbonyl group, a N-aralkylcarbamoyl group and a N-cycloalkylcarbamoyl group having 3 to 6 cycloalkyl carbon atoms.

As the above acyl group, there may be mentioned, for example, a lower alkanoyl group such as formyl, acetyl, propionyl, butyryl, isobutyryl, valeryl, isovaleryl, pivaloyl, hexanoyl, isopentylcarbonyl and trifluoroacetyl; an alkenoyl group having 3 to 6 carbon atoms such as acryloyl, methacryloyl and crotonoyl; a cycloalkylcarbonyl having 4 to 7 cycloalkyl carbon atoms such as cyclopentylcarbonyl and cyclohexylcarbonyl; an aroyl group such as benzoyl, toluoyl, naphthoyl and phthaloyl; an arylalkanoyl group such as phenylacetyl, phenylbutyryl and phenylhexanoyl; a hetero monocyclic carbonyl group such as morpholinocarbonyl, furoyl, thenoyl, nicotinoyl and isonicotinoyl; a condensed heterocyclic carbonyl group such as quinolylcarbonyl and indolylcarbonyl; a hetero monocyclic alkanoyl group such as morpholinoacetyl, furylacetyl, thienylacetyl and thienylpropionyl; and a condensed heterocyclic alkanoyl group such as indolylacetyl and acridinylacetyl.

As the above alkoxycarbonyl group of $R^1$, there may be mentioned, for example, methoxycarbonyl, ethoxycarbonyl, isopropoxycarbonyl, t-butoxycarbonyl (Boc) and isopentyloxycarbonyl; and as the aralkyloxycarbonyl group, there may be mentioned, for example, benzyloxycarbonyl, phenethyloxycarbonyl and 4-nitrobenzyloxycarbonyl.

As the above N-alkylcarbamoyl group, there may be mentioned, for example, N-methylcarbamoyl, N-ethylcarbamoyl, N-t-butylcarbamoyl and N-isopentylcarbamoyl; as the N-cycloalkylcarbamoyl group, there may be mentioned, for example, N-cyclopentylcarbamoyl and N-cyclohexylcarbamoyl, and there may be also used a N-arylcarbamoyl group such as N-phenylcarbamoyl; and a N-aralkylcarbamoyl group such as N-benzylcarbamoyl.

Further, as a protective group for the terminal amino group of $R^1$, there may be used a lower alkanesulfonyl group such as methanesulfonyl and ethanesulfonyl; and an allenesulfonyl group such as benzenesulfonyl, tosyl and mesitylsulfonyl.

A preferred protective group for the terminal amino group of $R^1$ is a lower alkanoyl group, a cycloalkanoyl group, an aroyl group, an alkoxycarbonyl group, an aralkyloxycarbonyl group, a N-alkylcarbamoyl group or a N-cycloalkylcarbamoyl group, more specifically an alkanoyl group having 1 to 6 carbon atoms, a cycloalkanoyl group having 4 to 7 carbon atoms, an alkoxycarbonyl group having 1 to 6 alkoxy carbon atoms, an aralkyloxycarbonyl group, a N-alkylcarbamoyl group having 1 to 5 alkyl carbon atoms or a N-cycloalkylcarbamoyl group having 3 to 6 cycloalkyl carbon atoms.

A particularly preferred $R^1$ may include a t-butylcarbamoyl, isopentylcarbamoyl, cyclopentylcarbamoyl, isopentylcarbonyl, cyclopentylcarbonyl, t-butoxycarbonyl, benzoyl or benzyloxycarbonyl.

A preferred group of $R^2$ is a phenyl group which may be substituted by one or two of a lower alkyl group, halogen atom, hydroxyl group which may be protected or perhalo lower alkyl group, more preferably a phenyl group, a substituted phenyl group substituted by one or two substituents selected from the group consisting of an alkyl group having 1 to 4 carbon atoms, halogen atom, hydroxyl group which may be protected, or perhalo alkyl group having 1 to 4 carbon atoms. As the lower alkyl group, there may be mentioned a straight or branched alkyl group such as methyl, ethyl, propyl, butyl, isobutyl, t-butyl, pentyl and hexyl, and as the halogen atom, there may be mentioned chlorine, bromine, iodine and fluorine. As a protective group for the hydroxyl group which may be protected, there may be used those described above as the substituent (e) in the case where the side chain of the amino acid of A is a hydroxyl group, and a benzyl group is particularly preferred. As a perhalo lower alkyl group, there may be mentioned a trifluoromethyl.

A particularly preferred $R^2$ may include a phenyl, 2-fluorophenyl, 4-fluorophenyl, 2-methylphenyl, 3-methylphenyl, 4-methylphenyl, 2,4-dimethylphenyl, 2,5-dimethylphenyl or 2-(trifluoromethyl)phenyl.

As a protective group for the terminal carboxyl group of $R^3$, there may be used those described above as the amidated carboxyl group (b) and the esterified carboxyl group (c) of the α-amino acid of A, and particularly preferred is that $R^3$ represents a formula of $-OR^4$ or a formula of $N(R^5)(R^6)$ where protective groups $R^4$, $R^5$ and $R^6$ each represent a substituted or unsubstituted lower alkyl group preferably having 1 to 4 carbon atoms or an aralkyl group, or $R^5$ and $R^6$ may be bonded with a nitrogen atom to which they are bonded, to form a hetero saturated monocyclic ring.

A particularly preferred example of $R^4$ is an aralkyl group such as benzyl. A particularly preferred example of $R^5$ is a lower alkyl group which is unsubstituted or substituted by hydroxy or aralkyloxy, such as methyl, ethyl, isobutyl, 2-hydroxyethyl, 2-benzyloxyethyl, 2-(4-fluorobenzyloxy)-ethyl, 2-(3-pyridylmethyl)oxyethyl, 2-benzylhydryloxyethyl, 2-(2-naphthylmethyl)oxyethyl; and an aralkyl group which is unsubstituted or substituted by a halogen or an alkoxy having 1 to 6 carbon atoms, such as benzyl, 4-fluorobenzyl, 2,4-dimethoxybenzyl and phenethyl. A particularly preferred example of $R^6$ is a hydrogen atom. Also, the group $R^3$ is a group in which $R^5$ and $R^6$ are bonded with a nitrogen atom to which they are bonded, to form a hetero saturated monocyclic ring, such as morpholino, pyrrolidine-1-yl, pyrazolidin-1-yl and piperidino.

Of these, a particularly preferred is that $R^4$ is an aralkyl group; or $R^5$ is an alkyl group having 1 to 4 carbon atoms which may be substituted by a hydroxy or aralkyloxy group, or an aralkyl group having which may be substituted by a halogen or a lower alkoxy group having 1 to 4 carbon atoms and $R^6$ is a hydrogen atom.

A particularly preferred $R^3$ may include a benzyl ester (OBzl), amino, methylamino, isobutylamino, 2-benzyloxyethylamino, 2,4-dimethoxybenzylamino, 2-(2-naphthylmethyl)-oxyethylamino, 2-(3-pyridylmethyl)oxyethylamino, 2-benzhydryloxyethylamino or morpholino.

As a salt of the azapeptide derivative represented by the above formula (I), there may be mentioned an acid addition salt and a basic salt. As the acid addition salt, there may be mentioned a salt of an inorganic acid (e.g., hydrochloric acid, sulfuric acid and phosphoric acid) or an organic acid (e.g., acetic acid, propionic acid, citric acid, tartaric acid, malic acid, oxalic acid and methanesulfonic acid); and as the basic salt, there may be mentioned a pharmaceutically acceptable salt such as a sodium salt, a potassium salt, an ammonium salt and an amine salt.

The azapeptide derivative (I) of the present invention can be prepared by a method conventionally used in peptide chemistry, for example, a method described in Schroder and Libke, "The Peptides", Vol. 1, Academic Press, New York, U.S.A. (1965) or Nobuo Izumiya, et al., "Fundamental and Experiment of Peptide Synthesis", Maruzen Co. (1985), and can be prepared by either the solution synthesis or the solid synthesis. Further, protected azaphenylalanine which is a starting material can be prepared by a known method found in the following literatures, and synthetic examples are described below in Reference examples.

Dutta, A. S., et al., J. Chem. Soc., Perkin Trancs. 1 (1975) p. 712

Pinnen, F., et al., J. C. S. Perkin I (1993) pp. 819 to 824 (Boc-AzPhe-ONp)

As a condensation method for forming a peptide bond, there may be mentioned an azide method, an acid chloride method, an acid anhydride method, a mixed acid anhydride method, a carbodiimide method, a carbodiimide additive method, an active ester method, a carbonyldiimidazole method, an oxidation reduction method and a method of using Woodward reagent K.

Before carrying out a condensation reaction, by a known means, a carboxyl group and an amino group which do not participate in the reaction may be protected, or a carboxyl group and an amino group which participate in the reaction may be activated.

As an activated carboxyl group, there may be mentioned, for example, a corresponding acid anhydride; azide; and an active ester with an alcohol, for example, pentachlorophenol, 2,4-dinitrophenol, cyanomethyl alcohol, 4-nitrophenol, N-hydroxy-5-norbornen-2,3-dicarboxyimide, N-hydroxysuccinimide or 1-hydroxybenzotriazole. As an activated amino group, there may be mentioned, for example, a corresponding phosphoric acid amide.

The reaction is carried out generally in a solvent and can be carried out, for example, in a solvent such as chloroform, dichloromethane, ethyl acetate, N,N-dimethylformamide, dimethyl sulfoxide, pyridine, dioxane, tetrahydrofuran, water and methanol, or a mixture thereof. The reaction can be carried out generally at a temperature range of about −30° C. to about 50° C.

A reaction of eliminating the protective group for the peptide varies depending on the kind of the protective group used, but it is required to remove the protective group without exerting influence on the peptide bond. As a method of eliminating the protective group, there may be mentioned, for example, acid treatment with hydrogen chloride, hydrogen bromide, anhydrous hydrogen fluoride, methanesulfonic acid, trifluoromethanesulfonic acid, trifluoroacetic acid or a mixture thereof. In addition thereto, there may be mentioned reduction by sodium or palladium carbon in liquid ammonia. In a deprotection reaction by the above acid treatment, it is effective to add a cation-capturing agent such as anisole, phenol and thioanisole.

After completion of the reaction, the azapeptide derivative of the present invention thus prepared can be obtained by a means known per se for separating a peptide, for example, extraction, partition, reprecipitation, recrystallization or column chromatography.

Further, the azapeptide derivative of the present invention can be converted into a pharmaceutically acceptable salt thereof by a method known per se.

The azapeptide derivative of the present invention exhibits a potent antagonistic activity in a test of controlling NKA constriction in hamster respiratory tracts. Also, said derivative is useful as an agent for curing pathology depending on NKA, particularly useful as an agent for curing nervous inflammation of respiratory apparatus, asthma and bronchospasm.

The toxicity of the azapeptide derivative of the present invention is extremely low, and even when an amount significantly exceeding an effective dose was used, there was no case of death.

The effective dose per day of the azapeptide derivative of the present invention is 0.01 to 100 mg, preferably 0.1 to 50 mg per 1 kg of body weight of a mammal.

In administration for a therapeutic purpose, the azapeptide derivative of the present invention is used as a medical composition in which said derivative or a salt thereof as an active ingredient is formulated with a pharmaceutically acceptable carrier, for example, an organic or inorganic and solid or liquid excipient suitable for oral administration, parenteral administration, external administration or inhalation. The above medical composition can be in the form of a capsule, a tablet, a sugar-coated tablet, a granule, a liquid, a suspension or an emulsion. If necessary, it is possible to add an aid, a stabilizer, a humectant, an emulsifier, a buffer or other conventionally used additive to the above preparation.

In the present specification, the term "lower" generally means 1 to 6 carbon atoms, preferably 1 to 4 carbon atoms otherwise specifically mentioned.

EXAMPLES

Synthetic examples of the azapeptide derivative of the present invention are described in detail by referring to Examples.

In the present specification, an amino acid, a peptide, a protective group, a solvent and so forth are represented by abbreviations conventionally used in this field of the art or the following abbreviations used by the IUPAC-IUB nomenclature committee. The abbreviation of α-azaamino acid is represented by adding a prefix "Az" to a corresponding amino acid, for example, AzPhe represents α-azaphenylalanine.

AzPhe: α-aza-phenylalanine
AzPhe(4-F): α-aza-4-fluoro-phenylalanine
AzPhe(2-Me): α-aza-2-methyl-phenylalanine
AzPhe(3-Me): α-aza-3-methyl-phenylalanine
AzPhe(4-Me): α-aza-4-methyl-phenylalanine
AzPhe(4-iPr): α-aza-4-isopropyl-phenylalanine
AzPhe(2,4-diMe): α-aza-2,4-dimethyl-phenylalanine
AzPhe(2,5-diMe): α-aza-2,5-dimethyl-phenylalanine
AzPhe(2-F): α-aza-2-fluoro-phenylalanine
AzPhe (2-CF$_3$): α-aza-2-(trifluoromethyl)-phenylalanine
AzTyr: α-aza-tyrosine
Asn: asparagine
Asp: aspartic acid
Arg: arginine
Cit: citrulline
Gln: glutamine
Met: methionine
Met(O$_2$): methioninesulfone
Orn: ornithine
Trp: tryptophan
Ph: phenyl
Boc: t-butoxycarbonyl
Z: benzyloxycarbonyl
Bz: benzoyl
OBzl: benzyl ester
OSu: N-hydroxysuccinimide ester
Dmob: 2,4-dimethoxybenzyl
ONp: 4-nitrophenyl ester
ONo: 2-nitrophenyl ester
DCC: N,N'-dicyclohexylcarbodiimide
DCUrea: N,N'-dicyclohexylurea
HOBt: 1-hydroxybenzotriazole
Et$_3$N: triethylamine
M: morpholino
NMM: N-methylmorpholine
TFA: trifluoroacetic acid
AcOEt: ethyl acetate
CH$_2$Cl$_2$: methylene chloride
DMF: N,N-dimethylformamide
MeOH: methanol
THF: tetrahydrofuran In the respective Examples, the following developing solvents were used in thin layer chromatography, and TLC plate silica gel 60F$_{254}$ (trade name) produced by Merck Co. was used.
Rf$_1$: chloroform-methanol-acetic acid-water (80:20:2.5:5) lower layer
Rf$_2$: chloroform-methanol (10:1)
Rf$_3$: chloroform-acetone (5:1)
Rf$_4$: ethyl acetate-hexane (2:1)
Rf$_5$: ethyl acetate-hexane (1:1)

Reference example 1
Synthesis of Boc-AzPhe-NHDmob

In 150 ml of acetonitrile was dissolved 6.80 g of 2,4-dimethoxybenzylamine hydrochloride, and 4.80 ml of Et$_3$N and 13.00 g of Boc-AzPhe-ONp were added to the solution. The mixture was refluxed under heating for 31 hours. The solvent was removed, and the residue was dissolved in AcOEt, washed successively with diluted hydrochloric acid, a saturated sodium hydrogen carbonate solution and a saturated saline solution, and then dried over anhydrous sodium sulfate. After the solvent was removed, the residue was purified by silica gel column chromatography using AcOEt-hexane to obtain the title compound.

Yield: 9.44 g; Rf$_3$: 0.52, Rf$_5$: 0.27; NMR (δ, DMSO-d$_6$, 55° C.): 1.34 (9H, s), 3.74 (3H, s), 3.78 (3H, s), 4.17 (2H, d, J=6 Hz), 4.54 (2H, br s), 6.42 to 6.53 (3H, m), 7.10 to 7.32 (6H, m), 8.72 (1H, br)

Reference example 2
Boc-AzPhe-NH(CH$_2$)$_2$OCH$_2$Ph

In the same manner as in Reference example 1, the title compound was obtained from 14.92 g of 2-benzyloxyethylamine hydrochloride, 16.60 ml of Et$_3$N and 15.39 g of Boc-AzPhe-ONp.

Yield: 13.60 g; Rf$_3$: 0.42, Rf$_5$: 0.22; NMR (δ, DMSO-d$_6$, 55° C.): 1.33 (9H, s), 3.28 (2H, td, J=6 Hz, 6 Hz), 3.47 (2H, t, J=6 Hz), 4.48 (2H, s), 4.53 (2H, br s), 6.32 (1H, br), 7.23 to 7.32 (10H, m), 8.69 (1H, br)

Reference example 3
Boc-AzPhe-NHCH$_2$Ph(4-F)

In the same manner as in Reference example 1, the title compound was obtained from 0.60 ml of 4-fluorobenzylamine, 0.72 ml of Et$_3$N and 2.00 g of Boc-AzPhe-ONp.

Yield: 1.47 g; Rf$_3$: 0.45, Rf$_5$: 0.30; NMR (δ, CDCl$_3$, 55° C.): 1.41 (9H, s), 4.42 (2H, d, J=6 Hz), 4.74 (2H, br s), 5.67 (1H, br), 5.87 (1H, br s), 6.96 to 7.15 (2H, m), 7.24 to 7.35 (7H, m)

Reference example 4
Boc-AzPhe-NH(CH$_2$)$_2$OCH$_2$Ph(4-F)

In the same manner as in Reference example 1, the title compound was obtained from 2.47 g of 2-(4-fluorobenzyloxy)-ethylamine hydrochloride, 2.52 ml of Et$_3$N and 2.33 g of Boc-AzPhe-ONp.

Yield: 2.49 g; Rf$_3$: 0.38, Rf$_4$: 0.30; NMR (δ, CDCl$_3$, 55° C.): 1.42 (9H, s), 3.45 to 3.49 (2H, m), 3.56 (2H, t, J=5 Hz), 4.47 (2H, s), 4.71 (2H, br s), 5.70 (1H, br), 5.88 (1H, br s), 6.96 to 7.03 (2H, m), 7.23 to 7.34 (7H, m)

Reference example 5
Boc-AzPhe-NH(CH$_2$)$_2$Ph

In the same manner as in Reference example 1, the title compound was obtained from 0.94 ml of β-phenethylamine and 1.50 g of Boc-AzPhe-ONp.

Yield: 1.20 g; Rf$_3$: 0.51, Rf$_5$: 0.32; NMR (δ, CDCl$_3$, 55° C.): 1.42 (9H, s), 2.83 (2H, t, J=7 Hz), 3.49 to 3.55 (2H, m), 4.71 (2H, br s), 5.38 (1H, br), 5.77 (1H, br s), 7.16 to 7.35 (10H, m)

Reference example 6
Boc-AzPhe-M

In the same manner as in Reference example 1, the title compound was obtained from 0.68 ml of morpholine, 0.54 ml of Et$_3$N and 1.50 g of Boc-AzPhe-ONp.

Yield: 1.10 g; Rf$_3$: 0.34, Rf$_5$: 0.15; NMR (δ, CDCl$_3$): 1.44 (9H, s), 3.44 (4H, t, J=5 Hz), 3.68 (4H, t, J=5 Hz), 4.51 (2H, br), 6.27 (1H, br), 7.28 to 7.38 (5H, m)

Reference example 7
Boc-AzPhe-OBzl

In 100 ml of THF was dissolved 12.16 g of t-butyl 3-benzylcarbazate, and 50 ml of a THF solution containing 13.63 g of N-carbobenzoxysuccinimide and 7.62 ml of Et$_3$N were added to the solution. The mixture was refluxed under heating for 18 hours. The solvent was removed, and the residue was dissolved in AcOEt, washed successively with diluted hydrochloric acid, a saturated sodium hydrogen carbonate solution and a saturated saline solution, and then dried over anhydrous sodium sulfate. After the solvent was removed, the residue was purified by silica gel column chromatography using AcOEt-hexane to obtain the title compound.

Yield: 12.81 g; $Rf_3$: 0.62, $Rf_5$: 0.54; NMR ($\delta$, $CDCl_3$, 55° C.): 1.39 (9H, s), 4.68 (2H, br s), 5.20 (2H, s), 6.20 (1H, br), 7.23 to 7.34 (10H, m)

Reference example 8
Boc-AzPhe-NHCH$_2$Ph

In 20 ml of acetonitrile were dissolved 1.50 g of t-butyl 3-benzylcarbazate and 0.83 ml of benzyl isocyanate, and the solution was refluxed under heating for 20 hours. Subsequent procedures were carried out in the same manner as in Reference example 7 to obtain the title compound.

Yield: 2.27 g; $Rf_3$: 0.46, $Rf_5$: 0.33; NMR ($\delta$, $CDCl_3$, 55° C.): 1.42 (9H, s), 4.46 (2H, d, J=6 Hz), 4.75 (2H, br s), 5.67 (1H, br), 5.86 (1H, br s), 7.23 to 7.35 (10H, m)

Reference example 9
Boc-AzPhe-NHCH$_3$

In 20 ml of acetonitrile were dissolved 456 mg of methylamine hydrochloride, 0.94 ml of Et$_3$N and 1.09 g of carbodiimidazole, and the solution was refluxed under heating for 20 hours. Thereafter, to the mixture were added 1.50 g of t-butyl 3-benzylcarbazate and 0.94 ml of Et$_3$N, and the mixture was refluxed under heating for 96 hours. Subsequent procedures were carried out in the same manner as in Reference example 7 to obtain the title compound.

Yield: 1.50 g; $Rf_3$: 0.24, $Rf_5$: 0.10; NMR ($\delta$, $CDCl_3$, 55° C.): 1.44 (9H, s), 2.83 (3H, s), 4.72 (2H, br s), 5.28 (1H, br), 5.86 (1H, br s), 7.25 to 7.35 (5H, m)

Reference example 10
Boc-AzPhe-NHCH$_2$CH(CH$_3$)$_2$

In 50 ml of acetonitrile were dissolved 0.67 ml of isobutylamine, 1.10 g of carbodiimidazole and 1.50 g of t-butyl 3-benzylcarbazate, and the solution was refluxed under heating for 20 hours. Subsequent procedures were carried out in the same manner as in Reference example 7 to obtain the title compound.

Yield: 1.64 g; $Rf_3$: 0.48, $Rf_5$: 0.34; NMR ($\delta$, $CDCl_3$, 55° C.): 0.91 (6H, d, J=7 Hz), 1.45 (9H, s), 1.71 to 1.84 (1H, m), 3.09 (2H, t, J=6 Hz), 4.71 (2H, br s), 5.41 (1H, br), 5.86 (1H, br s), 7.25 to 7.35 (5H, m)

Reference example 11
Boc-AzPhe (4-F)-NH(CH$_2$)$_2$OCH$_2$Ph
(1) Boc-AzPhe(4-F)-ONp In 50 ml of THF was dissolved 12.00 g of 4-nitrophenyl chloroformate, and 14.40 g of t-butyl 3-(4-fluorobenzyl)-carbazate and 6.60 ml of NMM were added to the solution under ice cooling. The mixture was stirred at room temperature for 18 hours. The solvent was removed, and the residue was dissolved in AcOEt, washed successively with diluted hydrochloric acid, a saturated sodium hydrogen carbonate solution and a saturated saline solution, and then dried over anhydrous sodium sulfate. After the solvent was removed, the residue was purified by silica gel column chromatography using AcOEt-hexane to obtain the title compound.

Yield: 19.50 g; $Rf_3$: 0.60, $Rf_5$: 0.52; NMR ($\delta$, DMSO-$d_6$, 55° C.): 1.38 (9H, s), 4.64 (2H, br s), 7.14 to 7.43 (6H, m), 8.30 (2H, d, J=9 Hz), 9.54 (1H, br)

(2) Boc-Azphe(4-F)-NH(CH$_2$)$_2$OCH$_2$Ph

In the same manner as in Reference example 1, the title compound was obtained from 627 mg of 2-benzyloxyethylamine hydrochloride and 1.40 g of Boc-AzPhe(4-F)-ONp.

Yield: 940 mg; $Rf_3$: 0.38, $Rf_4$: 0.33; NMR ($\delta$, DMSO-$d_6$, 55° C.): 1.31 (9H, s), 3.25 (2H, td, J=6 Hz, 6 Hz), 3.45 (2H, t, J=6 Hz), 4.46 (2H, s), 4.49 (2H, br s), 6.31 (1H, br), 7.03 to 7.30 (9H, m), 8.67 (1H, br)

Reference example 12
Boc-AzTyr(CH$_2$Ph)-NHDmob
(1) Boc-AzTyr-ONp

In the same manner as in Reference example 11 (1), the title compound was obtained from 2.86 g of 4-nitrophenyl chloroformate, 1.54 ml of NMM and 4.00 g of t-butyl 3-(4-hydroxybenzyl)carbazate.

Yield: 4.55 g; $Rf_3$: 0.36, $Rf_5$: 0.34; NMR ($\delta$, DMSO-$d_6$, 55° C.): 1.38 (9H, s), 4.54 (2H, br), 6.74 (2H, d, J=8 Hz), 7.15 (2H, d, J=8 Hz), 7.37 (2H, d, J=9 Hz), 8.29 (2H, d, J=9 Hz), 9.19 (1H, s), 9.44 (1H, br)

(2) Boc-AzTyr-NHDmob

In the same manner as in Reference example 1, the title compound was obtained from 2.20 g of 2,4-dimethoxybenzylamine hydrochloride, 1.54 ml of Et$_3$N and 4.04 g of Boc-AzTyr-ONp.

Yield: 3.63 g; $Rf_3$: 0.23, $Rf_4$: 0.28; NMR ($\delta$, $CDCl_3$, 55° C.): 1.40 (9H, s), 3.77 (3H, s), 3.78 (3H, s), 4.36 (2H, s), 4.62 (2H, br), 5.83 (2H, br), 6.41 to 6.44 (2H, m), 6.74 to 6.78 (2H, m), 7.09 to 7.20 (3H, m)

(3) Boc-AzTyr(CH$_2$Ph)-NHDmob

In 5 ml of DMF was dissolved 3.16 g of Boc-AzTyr-NHDmob, and 2.00 g of potassium carbonate and 1.38 g of benzyl bromide were added to the solution. The mixture was stirred at room temperature for 12 hours. The solvent was removed, and the residue was dissolved in AcOEt, washed successively with diluted hydrochloric acid, a saturated sodium hydrogen carbonate solution and a saturated saline solution, and then dried over anhydrous sodium sulfate. After the solvent was removed, the residue was purified by silica gel column chromatography using AcOEt-hexane to obtain the title compound.

Yield: 3.00 g; $Rf_3$: 0.53, $Rf_4$: 0.42; NMR ($\delta$, $CDCl_3$, 55° C.): 1.40 (9H, s), 3.78 (6H, s), 4.36 (2H, s), 4.64 (2H, br), 5.05 (2H, s), 5.82 (2H, br), 6.41 to 6.44 (2H, m), 6.90 to 7.41 (10H, m)

Reference example 13
peptide III: Ac-Leu-Asp-Gln-Trp-Phe-Gly-NH$_2$

As a comparative compound, the title compound was synthesized.

Reference example 14
Boc-Asp(OBzl)-Gln-Trp-Phe-NH$_2$

As a comparative compound, the title compound was synthesized.

Reference example 15
Boc-Azphe(2-Me)-NH(CH$_2$)$_2$OCH$_2$Ph
(1) PhCH$_2$O(CH$_2$)$_2$NHCO$_2$Np In 300 ml of THF was dissolved 40.40 g of 2-benzyloxyethylamine 4-toluenesulfonate, and 35.00 ml of Et$_3$N and 25.00 g of 4-nitrophenyl chloroformate were added to the solution under ice cooling. The mixture was stirred at room temperature for 1 hour, and then the solvent was removed. The residue was dissolved in AcOEt, washed with a saturated saline solution and then dried over anhydrous sodium sulfate. After the solvent was removed, the residue was purified by silica gel column chromatography using AcOEt-hexane to obtain the title compound.

Yield: 37.70 g; NMR (δ, CDCl$_3$): 3.51 (2H, td, J=5 Hz, 5 Hz), 3.64 (2H, t, J=5 Hz), 4.57 (2H, s), 5.52 (1H, br), 7.28 to 7.41 (7H, m), 8.21 to 8.27 (2H, m)

(2) Boc-AzPhe(2-Me)-NH(CH$_2$)$_2$OCH$_2$Ph

In 30 ml of THF was dissolved 3.00 g of t-butyl 3-(2-methylbenzyl)carbazate, and 4.00 g of PhCH$_2$O(CH$_2$)$_2$NHCO$_2$Np and 2.00 ml of Et$_3$N were added to the solution. The mixture was stirred at room temperature for 18 hours, and then the solvent was removed. Subsequent procedures were carried out in the same manner as in Reference example 7 to obtain the title compound.

Yield: 4.62 g; Rf$_3$: 0.45, Rf$_5$: 0.21; NMR (δ, CDCl$_3$, 55° C.): 1.41 (9H, s), 2.31 (3H, s), 3.45 to 3.50 (2H, m), 3.55 to 3.60 (2H, m), 4.51 (2H, s), 4.77 (2H, br), 5.75 (2H, br), 7.13 to 7.29 (9H, m)

Reference example 16
Boc-AzPhe(3-Me)-NH(CH$_2$)$_2$OCH$_2$Ph

In 30 ml of THF was dissolved 3.00 g of t-butyl 3-(3-methylbenzyl)carbazate, and 4.00 g of PhCH$_2$O(CH$_2$)$_2$NHCO$_2$Np and 2.00 ml of Et$_3$N were added to the solution. The mixture was stirred at room temperature for 18 hours, and then the solvent was removed. Subsequent procedures were carried out in the same manner as in Reference example 7 to obtain the title compound.

Yield: 5.15 g; Rf$_3$: 0.46, Rf$_5$: 0.22; NMR (δ, CDCl$_3$, 55° C.): 1.43 (9H, s), 2.33 (3H, s), 3.47 (2H, td, J=5 Hz, 5 Hz), 3.58 (2H, t, J=5 Hz), 4.51 (2H, s), 4.68 (2H, br), 5.72 (1H, br), 5.84 (1H, br s), 7.03 to 7.09 (9H, m)

Reference example 17
Boc-AzPhe(4-Me)-NH(CH$_2$)$_2$OCH$_2$Ph

In 30 ml of THF was dissolved 3.00 g of t-butyl 3-(4-methylbenzyl)carbazate, and 4.00 g of PhCH$_2$O(CH$_2$)$_2$NHCO$_2$Np and 2.00 ml of Et$_3$N were added to the solution. The mixture was stirred at room temperature for 18 hours, and then the solvent was removed. Subsequent procedures were carried out in the same manner as in Reference example 7 to obtain the title compound.

Yield: 4.94 g; Rf$_3$: 0.46, Rf$_5$: 0.22; NMR (δ, CDCl$_3$, 55° C.): 1.43 (9H, s), 2.33 (3H, s), 3.45 to 3.49 (2H, m), 3.55 to 3.59 (2H, m), 4.50 (2H, s), 4.67 (2H, br), 5.71 (1H, br), 5.82 (1H, br s), 7.13 to 7.29 (9H, m)

Reference example 18
Boc-AzPhe(4-iPr)-NH(CH2)$_2$OCH$_2$Ph

In 30 ml of THF was dissolved 3.34 g of t-butyl 3-(4-isopropylbenzyl)carbazate, and 4.00 g of PhCH$_2$O(CH2)$_2$NHCO$_2$Np and 2.00 ml of Et$_3$N were added to the solution. The mixture was stirred at room temperature for 18 hours, and then the solvent was removed. Subsequent procedures were carried out in the same manner as in Reference example 7 to obtain the title compound.

Yield: 5.61 g; Rf$_3$: 0.47, Rf$_5$: 0.23; NMR (δ, CDCl$_3$, 55° C.): 1.23 (3H, s), 1.25 (3H, s), 1.42 (9H, s), 2.89 (1H, septet, J=7 Hz), 3.46 (2H, td, J=5 Hz, 5 Hz), 3.57 (2H, t, J=5 Hz), 4.50 (2H, s), 4.67 (2H, br), 5.70 (1H, br), 5.87 (1H, br s), 7.17 to 7.31 (9H, m)

Reference example 19
Boc-AzPhe(2,4-diMe)-NH(CH$_2$)$_2$OCH$_2$Ph (1) PhCH$_2$O(CH$_2$)$_2$NCO In 80 ml of AcOEt was dissolved 8.70 g of 3-benzyloxypropionic acid, and 6.80 ml of Et$_3$N and 5.10 ml of ethyl chlorocarbonate were added to the solution at −10° C., and the mixture was stirred for 15 minutes. Thereafter, 16 ml of an aqueous solution containing 4.78 g of sodium azide was added to the mixture, and the resulting mixture was stirred at −5° to 0° C. for 30 minutes. The reaction mixture was washed with water and dried over anhydrous magnesium sulfate. Into a flask in which 15 ml of AcOEt had been refluxed under heating, the AcOEt solution containing the acid azide was added dropwise over 20 minutes, and the mixture was further refluxed under heating for 10 minutes. After the solvent was removed, the residue was distilled under reduced pressure (97° C./4 mmHg) to obtain the title compound.

Yield: 6.40 g; NMR (δ, CDCl$_3$): 3.43 (2H, t, J=5 Hz), 3.61 (2H, t, J=5 Hz) 4.59 (2H, s), 7.26 to 7.37 (5H, m)

(2) Boc-AzPhe(2,4-diMe)-NH(CH$_2$)$_2$OCH$_2$Ph

In 20 ml of THF were dissolved 2.00 g of t-butyl 3-(2,4-dimethylbenzyl)carbazate and 1.40 g of PhCH$_2$O(CH$_2$)$_2$NCO, and the mixture was stirred at room temperature for 18 hours. Subsequent procedures were carried out in the same manner as in Reference example 7 to obtain the title compound.

Yield: 3.00 g; Rf$_3$: 0.46, Rf$_5$: 0.23; NMR (δ, CDCl$_3$, 55° C.) : 1.41 (9H, s), 2.27 (3H, s), 2.29 (3H, s), 3.47 (2H, td, J=5 Hz, 5 Hz), 3.57 (2H, t, J=5 Hz), 4.50 (2H, s), 4.73 (2H, br s), 5.70 to 5.74 (2H, m), 6.93 to 7.02 (3H, m), 7.24 to 7.31 (5H, m)

Reference example 20
Boc-AzPhe(2,5-diMe)-NH(CH$_2$)$_2$OCH$_2$Ph

In 20 ml of THF were dissolved 2.00 g of t-butyl 3-(2,5-dimethylbenzyl)carbazate and 1.40 g of PhCH$_2$O(CH$_2$)$_2$NCO, and the mixture was stirred at room temperature for 18 hours. Subsequent procedures were carried out in the same manner as in Reference example 7 to obtain the title compound.

Yield: 3.07 g; Rf$_3$: 0.46, Rf$_5$: 0.23; NMR (δ, CDCl$_3$, 55° C.): 1.41 (9H, s), 2.26 (3H, s), 2.28 (3H, s), 3.47 (2H, td, J=5 Hz, 5 Hz), 3.58 (2H, t, J=5 Hz), 4.51 (2H, s), 4.73 (2H, br s), 5.71 to 5.77 (2H, m), 6.94 to 7.06 (3H, m), 7.24 to 7.31 (5H, m)

Reference example 21
Boc-Trp-NHNHCH$_2$Ph(2-F)

In 30 ml of MeOH were dissolved 3.00 g of Boc-Trp-NHNH$_2$ and 1.23 g of 2-fluorobenzaldehyde, the mixture was stirred at room temperature for 18 hours, and then the solvent was removed. The residue was dissolved again in 30 ml of THF, and the solution was stirred in the presence of 1.00 g of 10% palladium carbon for one week in a hydrogen stream. After palladium carbon was separated by filtration, the solvent was removed. The residue was purified by silica gel column chromatography using AcOEt-hexane to obtain the title compound.

Yield: 680 mg; Rf$_3$: 0.15, Rf$_4$: 0.25; [α]$_D$: −9.07 (C=1.19, DMF) NMR (δ, DMSO-d$_6$, 55° C.): 1.29 (9H, s), 2.87 (1H, dd, J=14 Hz, 8 Hz), 2.99 (1H, dd, J=14 Hz, 5 Hz), 3.81 to 3.92 (2H, m), 4.12 to 4.20 (1H, m), 5.11 to 5.17 (1H, m), 6.45 (1H, br), 6.93 to 7.56 (9H, m), 9.29 (1H, br), 10.65 (1H, br s)

Reference example 22
Boc-Trp-NHNHCH$_2$Ph(2-CF$_3$)

In 30 ml of MeOH were dissolved 3.00 g of Boc-Trp-NHNH$_2$ and 1.72 g of 2-(trifluoromethyl)benzaldehyde, the mixture was stirred at room temperature for 18 hours, and then the solvent was removed. The residue was dissolved again in 30 ml of THF, and the solution was stirred in the presence of 1.00 g of 10% palladium carbon for one week in a hydrogen stream (3.50 kg/cm$^2$). Subsequent procedures were carried out in the same manner as in Reference example 21 to obtain the title compound.

Yield: 1.56 g; $Rf_3$: 0.20, $Rf_4$: 0.33; $[\alpha]_D$: −8.39 (C=1.04, DMF) NMR ($\delta$, DMSO-$d_6$, 55° C.): 1.28 (9H, s), 2.86 (1H, dd, J=14 Hz, 8 Hz), 2.98 (1H, dd, J=14 Hz, 5 Hz), 4.01 to 4.04 (2H, m), 4.12 to 4.20 (1H, m), 5.22 to 5.28 (1H, m), 6.50 (1H, br), 6.93 to 7.73 (9H, m), 9.34 (1H, br), 10.65 (1H, br s)

Reference example 23

Boc-Trp-NHNHCH$_2$Ph

In 600 ml of MeOH were dissolved 60.00 g of Boc-Trp-NHNH$_2$ and 21.00 g of benzaldehyde, and the mixture was stirred in the presence of 3.80 g of 10% palladium carbon for 18 hours in a hydrogen stream. Subsequent procedures were carried out in the same manner as in Reference example 21 to obtain the title compound.

Yield: 68.90 g; $Rf_4$: 0.25; $[\alpha]_D$: −8.41 (C=1.20, DMF) NMR ($\delta$, DMSO-$d_6$, 55° C.): 1.29 (9H, s), 2.88 (1H, dd, J=15 Hz, 9 Hz), 3.00 (1H, dd, J=15 Hz, 5 Hz), 3.72 to 3.84 (2H, m), 4.13 to 4.20 (1H, m), 5.05 to 5.07 (1H, m), 6.47 (1H, br), 6.93 to 7.32 (9H, m), 9.24 (1H, br), 10.65 (1H, br s)

Reference example 24

Boc-AzPhe-NH(CH$_2$)$_2$O-(2-naphthylmethyl)

In the same manner as in Reference example 1, the title compound was obtained from 2.74 g of 2-(2-naphthylmethyl)-oxyethylamine, 1.90 ml of Et3N and 5.27 g of Boc-AzPhe-ONp.

Yield: 5.40 g; $Rf_3$: 0.43, $Rf_5$: 0.18; NMR ($\delta$, DMSO-$d_6$, 55° C.): 1.31 (9H, s), 3.31 (2H, td, J=6 Hz, 6 Hz), 3.53 (2H, t, J=6 Hz), 4.53 (2H, br s), 4.65 (2H, s), 6.35 (1H, br), 7.23 to 7.31 (5H, m), 7.46 to 7.52 (3H, m), 7.83 to 7.90 (4H, m), 8.68 (1H, br)

Example 1

Boc-Asp(OBzl)-Gln-Trp-AzPhe-NH$_2$ (1) Z-Trp-AzPhe-NHDmob

In MeOH was dissolved 11.60 g of Boc-AzPhe-NHDmob, and 5.31 g of 4-toluenesulfonic acid monohydrate was added to the solution. The mixture was refluxed under heating for 2 hours. The solvent was removed, and the residue was dissolved in AcOEt, washed successively with a 10% sodium carbonate solution and a saturated saline solution, and then dried over anhydrous sodium sulfate, and the solvent was removed. The residue was dried under reduced pressure and then dissolved in 50 ml of THF. The solution was added to Z-Trp-OH mixed acid anhydride prepared separately (obtained by dissolving 9.07 g of Z-Trp-OH in 80 ml of THF, adding 2.95 ml of NMM and 20 ml of a THF solution containing 3.48 ml of isobutyl chloroformate to the solution under ice cooling and stirring the mixture for 1 hour), and the mixture was stirred at room temperature for 18 hours. The solvent was removed, and the residue was dissolved in CH$_2$Cl$_2$, washed successively with diluted hydrochloric acid, a saturated sodium hydrogen carbonate aqueous solution and a saturated saline solution, and then dried over anhydrous sodium sulfate. After the solvent was removed, the residue was purified by silica gel column chromatography using AcOEt-hexane to obtain the title compound.

Yield: 10.34 g; $Rf_3$: 0.23, $Rf_4$: 0.24; $[\alpha]_D$: −20.74 (C=1.03, DMF) NMR ($\delta$, DMSO-$d_6$, 55° C.): 2.94 (1H, dd, J=14 Hz, 8 Hz), 3.04 (1H, dd, J=14 Hz, 6 Hz), 3.70 (2H, s), 3.74 (3H, s), 4.12 to 4.24 (4H, m), 4.66 (1H, d, J=14 Hz), 4.76 (1H, d, J=13 Hz), 4.83 (1H, d, J=13 Hz), 6.39 to 6.49 (3H, m), 6.92 to 7.54 (17H, m), 10.09 (1H, br s), 10.68 (1H, br s)

(2) Boc-Gln-Trp-AzPhe-NHDmob

In 150 ml of MEOH, 8.53 g of Z-Trp-AzPhe-NHDmob was stirred in the presence of 0.85 g of 10% palladium carbon for 18 hours in a hydrogen stream. After palladium carbon was separated by filtration, the solvent was removed. The residue was dried under reduced pressure and then dissolved in 70 ml of DMF. Under ice cooling, 4.93 g of Boc-Gln-ONp an d 1.48 ml of NMM were added to the solution, and the mixture was stirred at room temperature for 18 hours. DMF was removed, and the residue was dissolved in CH$_2$Cl$_2$, washed successively with diluted hydrochloric acid, a saturated sodium hydrogen carbonate aqueous solution and a saturated saline solution, and then dried over anhydrous sodium sulfate. After the solvent was removed, the residue was purified by silica gel column chromatography using MeOH-CH$_2$Cl$_2$ to obtain the title compound.

Yield: 6.94 g; $Rf_1$: 0.48, $Rf_2$: 0.14; $[\alpha]_D$: −15.00 (C=1.15, DMF) NMR ($\delta$, DMSO-$d_6$, 55° C.): 1.33 (9H, s), 1.58 to 1.82 (2H, m), 2.04 to 2.10 (2H, m), 2.95 to 3.13 (2H, m), 3.73 (3H, s), 3.76 (3H, s), 3.86 to 3.94 (1H, m), 4.09 to 4.15 (3H, m), 4.34 to 4.42 (1H, m), 4.61 (1H, d, J=14 Hz), 6.41 to 6.65 (5H, m), 6.93 to 7.53 (12H, m), 8.07 (1H, br s), 10.00 (1H, br s), 10.71 (1H, br s)

(3) Boc-Asp(OBzl)-Gln-Trp-AzPhe-NH$_2$

At water temperature, 4.00 g of Boc-Gln-Trp-Azphe-NHDmob was left to stand in 48.00 ml of a TFA-ethanedithioldimethyl sulfide (10:1:1) solution for 9 hours, and then TFA was removed. Ether was added to the residue to precipitate crystals, and the crystals were collected by filtration, dried under reduced pressure and then dissolved in 40 ml of DMF. Under ice cooling, 0.76 ml of Et$_3$N, 2.30 g of Boc-Asp(OBzl)-OSu and 0.60 ml of NMM were added to the solution, and the mixture was stirred at room temperature for 18 hours. The solvent was removed, and the residue was dissolved in 2-butanol-CH$_2$Cl$_2$ (5:1), washed successively with diluted hydrochloric acid, a saturated sodium hydrogen carbonate aqueous solution and a saturated saline solution, and then dried over anhydrous sodium sulfate. After the solvent was removed, the residue was purified by silica gel column chromatography using MeOH-CH$_2$Cl$_2$ to obtain the title compound.

Yield: 1.44 g; $Rf_1$: 0.39, $Rf_2$: 0.11; $[\alpha]_D$: −26.71 (C=1.21, DMF) FAB mass spectrum (M+1): 785 NMR ($\delta$, DMSO-$d_6$, 55° C.): 1.36 (9H, s), 1.69 to 1.91 (2H, m), 2.09 (2H, t, J=8 Hz), 2.60 (1H, dd, J=16 Hz, 9 Hz), 2.77 (1H, dd, J=16 Hz, 5 Hz), 2.96 (1H, dd, J=15 Hz, 7 Hz), 3.07 (1H, dd, J=15 Hz, 8 Hz), 4.06 (1H, d, J=15 Hz), 4.24 to 4.36 (3H, m), 4.59 (1H, d, J=15 Hz), 5.08 (2H, s), 5.78 (2H, br s), 6.58 (1H, br), 6.93 to 7.53 (17H, br), 7.75 (1H, d, J=8 Hz), 8.19 (1H, br s), 9.95 (1H, br s), 10.68 (1H, br s)

Example 2

Boc-Asp(OBzl)-Gln-Trp-AzPhe-NH(CH2)$_2$OCH$_2$Ph (1) Boc-Trp-AzPhe-NH(CH$_2$)$_2$OCH$_2$Ph

At room temperature, 815 mg of Boc-AzPhe-NH(CH$_2$)$_2$OCH$_2$Ph was left to stand in 5.00 ml of 4N HCl-AcOEt for 1 hour, and then the solvent was removed. The residue was dried under reduced pressure and then 5 ml of DMF and 0.28 ml of Et$_3$N was added to the solution. The solution was added to Boc-Trp-OH mixed acid anhydride prepared separately (obtained by dissolving 690 mg of Boc-Trp-OH in 5 ml of THF, adding 0.22 ml of NMM and 0.27 ml of isobutyl chloroformate to the solution under ice cooling and stirring the mixture for 1 hour), and the mixture was stirred at room temperature for 18 hours. The solvent was removed, and the residue was dissolved in AcOEt, washed successively with diluted hydrochloric acid, a saturated sodium hydrogen carbonate aqueous solution and a saturated saline solution, and then dried over anhydrous sodium sulfate. After the solvent was removed, the residue was purified by silica gel column chromatography using AcOEt-hexane to obtain the title compound.

Yield: 650 mg; $Rf_3$: 0.17, $Rf_4$: 0.21; $[\alpha]_D$: −8.31 (C=1.01, DMF) FAB mass spectrum (M+1): 586 NMR (δ, DMSO-$d_6$, 55° C.): 1.32 (9H, s), 2.91 (1H, dd, J=14 Hz, 8 Hz), 2.99 (1H, dd, J=14 Hz, 7 Hz), 3.20 to 3.31 (2H, m), 3.41 (2H, t, J=6 Hz), 4.08 to 4.15 (2H, m), 4.45 (2H, s), 4.62 (1H, d, J=15 Hz), 6.18 (1H, br), 6.91 to 7.52 (16H, m), 9.98 (1H, br s), 10.70 (1H, br s)

(2) Boc-Gln-Trp-AzPhe-NH(CH$_2$)$_2$OCH$_2$Ph

Under ice cooling, 750 mg of Boc-Trp-AzPhe-NH(CH$_2$)$_2$OCH$_2$Ph was left to stand in 3.20 ml of 4N HCl-AcOEt for 1 hour, and then the solvent was removed. The residue was dried under reduced pressure and then dissolved in 5 ml of DMF. Under ice cooling, 470 mg of Roc-Gln-ONp, 0.18 ml of Et$_3$N and 0.14 ml of NMM were added to the solution, and the mixture was stirred at room temperature for 18 hours. DMF was removed, and the residue was dissolved in CH$_2$Cl$_2$, washed successively with diluted hydrochloric acid, a saturated sodium hydrogen carbonate aqueous solution and a saturated saline solution, and then dried over anhydrous sodium sulfate. After the solvent was removed, the residue was purified by silica gel column chromatography using MeOH-CH$_2$Cl$_2$ to obtain the title compound.

Yield: 800 mg; $Rf_1$: 0.46, $Rf_2$: 0.12; $[\alpha]_D$: −19.19 (C=1.38, DMF) FAB mass spectrum (M+1): 714 NMR (δ, DMSO-$d_6$, 55° C.): 1.34 (9H, s), 1.66 to 1.86 (2H, m), 2.07 to 2.13 (2H, m), 2.95 to 3.14 (4H, m), 3.39 (2H, t, J=6 Hz), 3.90 to 3.97 (1H, m), 4.11 (1H, d, J=15 Hz), 4.34 to 4.41 (1H, m), 4.46 (2H, s), 4.57 (1H, d, J=15 Hz), 6.10 (1H, br), 6.57 to 6.75 (2H, br), 6.94 to 7.53 (16H, m), 8.08 (1H, br s), 9.97 (1H, br s), 10.74 (1H, br s)

(3) Boc-Asp(OBzl)-Gln-Trp-AzPhe-NH(CH$_2$)$_2$OCH$_2$Ph

In the same manner as in Example 2 (2), the title compound was obtained from 300 mg of Boc-Gln-Trp-AzPhe-NH(CH$_2$)$_2$OCH$_2$Ph, 1.50 ml of 4N HCl-AcOEt, 0.06 ml of Et$_3$N, 0.05 ml of NMM and 177 mg of Boc-Asp(OBzl)-OSu.

Yield: 230 mg; $Rf_1$: 0.50, $Rf_2$: 0.25; $[\alpha]_D$: −18.08 (C=1.15, DMF) FAB mass spectrum (M+1): 919 NMR (δ, DMSO-$d_6$, 55° C.): 1.36 (9H, s), 1.71 to 1.91 (2H, m), 2.10 (2H, t, J=8 Hz), 2.60 (1H, dd, J=16 Hz, 8 Hz), 2.78 (1H, dd, J=16 Hz, 4 Hz), 2.93 to 3.13 (4H, m), 3.38 (2H, t, J=6 Hz), 4.11 (1H, d, J=14 Hz), 4.25 to 4.36 (3H, m), 4.44 (2H, s), 4.54 (1H, d, J=14 Hz), 5.07 (2H, s), 6.04 (1H, br), 6.59 (1H, br), 6.92 to 7.52 (22H, m), 7.75 (1H, d, J=7 Hz), 8.21 (1H, br s), 9.95 (1H, br s), 10.71 (1H, br s)

Example 3
i-Pent-CO-Gln-Trp-AzPhe-NH(CH$_2$)$_2$OCH$_2$Ph (i-Pent: isopentyl)

In the same manner as in Example 2 (2), the title compound was obtained from 2.00 g of Boc-Gln-Trp-AzPhe-NH(CH2)$_2$OCH$_2$Ph, 7.00 ml of 4N HCl-AcOEt, 0.37 ml of Et$_3$N, 0.31 ml of NMM and 0.60 g of 4-methylvaleric acid N-hydroxysuccinimide ester.

Yield: 1.57 g; $Rf_1$: 0.46, $Rf_2$: 0.09; $[\alpha]_D$: −21.03 (C=1.49, DMF) FAB mass spectrum (M+1): 712 NMR (δ, DMSO-$d_6$, 55° C.): 0.84 (6H, d, J=6 Hz), 1.33 to 1.54 (3H, m), 1.68 to 1.92 (2H, m), 2.05 to 2.10 (4H, m), 2.94 to 3.10 (4H, m), 3.40 (2H, t, J=6 Hz), 4.11 to 4.25 (2H, m), 4.30 to 4.40 (1H, m), 4.46 (2H, s), 4.57 (1H, d, J=14 Hz), 6.10 (1H, br), 6.60 (1H, br), 6.95 to 7.52 (16H, m), 7.77 (1H, d, J=7 Hz), 8.06 (1H, br s), 9.93 (1H, br s), 10.73 (1H, br s)

Example 4
Bz-Gln-Trp-AzPhe-NH(CH$_2$)$_2$OCH$_2$Ph

In the same manner as in Example 2 (2), the title compound was obtained from 350 mg of Boc-Gln-Trp-AzPhe-NH(CH$_2$)$_2$OCH$_2$Ph, 1.50 ml of 4N HCl-AcOEt, 0.07 ml of Et$_3$N, 0.06 ml of NMM and 0.06 ml of benzoyl chloride.

Yield: 170 mg; $Rf_1$: 0.48, $Rf_2$: 0.16; $[\alpha]_D$: −13.35 (C=1.06, DMF) FAB mass spectrum (M+1): 718 NMR (δ, DMSO-$d_6$, 55° C.): 1.93 to 2.06 (2H, m), 2.21 (2H, t, J=8 Hz), 2.96 to 3.12 (4H, m), 3.38 (2H, t, J=6 Hz), 3.99 to 4.03 (1H, m), 4.14 (1H, d, J=15 Hz), 4.32 to 4.39 (1H, m), 4.41 (2H, s), 4.59 (1H, d, J=15 Hz), 6.15 (1H, br), 6.71 (1H, br), 6.92 to 7.83 (16H, m), 8.21 (1H, d, J=6 Hz), 8.52 (1H, d, J=7 Hz), 9.93 (1H, br s), 10.72 (1H, br s)

Example 5
cyPent-CO-Gln-Trp-AzPhe-NH(CH$_2$)$_2$OCH$_2$Ph (cyPent: cyclopentyl)

In the same manner as in Example 2 (2), the title compound was obtained from 350 mg of Boc-Gln-Trp-AzPhe-NH(CH$_2$)$_2$OCH$_2$Ph, 1.50 ml of 4N HCl-AcOEt, 0.07 ml of Et$_3$N and cyclopentanecarboxylic anhydride (prepared from 0.11 ml of cyclopentanecarboxylic acid and 101 mg of DCC).

Yield: 230 mg; $Rf_1$: 0.47, $Rf_2$: 0.14; $[\alpha]_D$: −26.39 (C=1.08, DMF) FAB mass spectrum (M+1): 710 NMR (δ, DMSO-$d_6$, 55° C.): 1.43 to 1.77 (8H, m), 1.79 to 1.92 (2H, m), 2.12 (2H, t, J=8 Hz), 2.55 to 2.60 (1H, m), 2.94 to 3.14 (4H, m), 3.14 (2H, t, J=6 Hz), 4.12 to 4.24 (2H, m), 4.31 to 4.38 (1H, m), 4.46 (2H, s), 4.58 (1H, d, J=15 Hz), 6.13 (1H, br s), 6.62 (1H, br s), 6.93 to 7.53 (16H, m), 7.71 (1H, d, J=5 Hz), 8.04 (1H, br s), 9.94 (1H, br s), 10.74 (1H, br s)

Example 6
t-Bu-NHCO-Gln-Trp-AzPhe-NH(CH$_2$)$_2$OCH$_2$Ph (t-Bu: t-butyl)

In the same manner as in Example 2 (2), the title compound was obtained from 350 mg of Boc-Gln-Trp-AzPhe-NH(CH$_2$)$_2$OCH$_2$Ph, 1.50 ml of 4N HCl-AcOEt, 0.07 ml of Et$_3$N and 0.06 ml of t-butyl isocyanate.

Yield: 270 mg; $Rf_1$: 0.48, $Rf_2$: 0.11; $[\alpha]_D$: −18.91 (C=1.00, DMF) FAB mass spectrum (M+1): 713 NMR (δ, DMSO-$d_6$, 55° C.): 1.18 (9H, s), 1.56 to 1.83 (2H, m), 2.07 (2H, t, J=8 Hz), 3.02 to 3.18 (4H, m), 3.40 (2H, t, J=6 Hz), 4.01 to 4.08 (1H, m), 4.14 (1H, d, J=15 Hz), 4.31 to 4.38 (1H, m), 4.46 (2H, s), 4.57 (1H, d, J=15 Hz), 5.82 to 5.86 (2H, m), 6.12 (1H, br), 6.57 (1H, br), 6.93 to 7.53 (16H, m), 8.17 (1H, d, J=6 Hz), 9.95 (1H, br s), 10.72 (1H, br s)

Example 7
i-Pent-NHCO-Gln-Trp-AzPhe-NH(CH$_2$)2OCH$_2$Ph (i-Pent: isopentyl)

In the same manner as in Example 2 (2), the title compound was obtained from 300 mg of Boc-Gln-Trp-AzPhe-NH(CH$_2$)$_2$OCH$_2$Ph, 1.50 ml of 4N HCl-AcOEt, 0.06 ml of Et$_3$N and isopentyl isocyanate (obtained by dissolving 0.05 ml of 4-methyl-valeric acid in 5 ml of toluene, adding 0.09 ml of diphenylphosphorylazide and 0.06 ml of Et$_3$N to the solution and stirring the mixture at 80° C. for 2 hours).

Yield: 120 mg; $Rf_1$: 0.49, $Rf_2$: 0.11; $[\alpha]_D$: −18.89 (C=1.15, DMF) NMR (δ, DMSO-$d_6$, 55° C.): 0.85 (6H, d, J=7 Hz), 1.25 (2H, td, J=7 Hz, 7 Hz), 1.49 to 1.85 (3H, m), 2.08 (2H, t, J=8 Hz), 2.93 to 3.20 (6H, m), 3.40 (2H, t, J=6 Hz), 4.05 to 4.19 (2H, m), 4.30 to 4.37 (1H, m), 4.46 (2H, s), 4.58 (1H, d, J=15 Hz), 5.90 to 5.95 (2H, m), 6.12 (1H, br), 6.57 (1H, br), 6.93 to 7.52 (16H, m), 8.19 (1H, br s), 9.96 (1H, br s), 10.71 (1H, br s)

Example 8
cyPent-NHCO-Gln-Trp-AzPhe-NH(CH$_2$)$_2$OCH$_2$Ph
(cyPent: cyclopentyl)

In the same manner as in Example 2 (2), the title compound was obtained from 300 mg of Boc-Gln-Trp-AzPhe-NH(CH$_2$)$_2$OCH$_2$Ph, 1.50 ml of 4N HCl-AcOEt, 0.06 ml of Et$_3$N and cyclopentyl isocyanate (obtained by dissolving 0.05 ml of cyclopentanecarboxylic acid in 5 ml of toluene, adding 0.09 ml of diphenylphosphorylazide and 0.06 ml of Et$_3$N to the solution and stirring the mixture at 80° C. for 2 hours).

Yield: 150 mg; Rf$_1$: 0.46, Rf$_2$: 0.11; [α]$_D$: −18.46 (C=1.00, DMF) NMR (δ, DMSO-d$_6$, 55° C.): 1.22 to 1.32 (2H, m), 1.44 to 1.82 (8H, m), 2.08 (2H, t, J=8 Hz), 2.96 to 3.15 (4H, m), 3.40 (2H, t, J=6 Hz), 3.76 to 3.83 (1H, m), 4.04 to 4.18 (2H, m), 4.30 to 4.36 (1H, m), 4.46 (2H, s), 4.57 (1H, d, J=15 Hz), 5.86 (1H, d, J=7 Hz), 5.98 (1H, br), 6.13 (1H, br), 6.59 (1H, br), 6.93 to 7.52 (16H, m), 8.21 (1H, br s), 9.98 (1H, br s), 10.72 (1H, br s)

Example 9
Boc-Met(O$_2$)-Trp-AzPhe-NH(CH$_2$)$_2$OCH$_2$Ph

Under ice cooling, 520 mg of Boc-Trp-AzPhe-NH(CH$_2$)$_2$OCH$_2$Ph was left to stand in 2.50 ml of 4N HCl-AcOEt for 1 hour, and then the solvent was removed. The residue was dried under reduced pressure and then dissolved in 10 ml of DMF. Under ice cooling, 0.18 ml of Et$_3$N, 250 mg of Boc-Met(O$_2$)-OH, 190 mg of DCC, 160 mg of HOBt and 0.14 ml of NMM were added to the solution, and the mixture was stirred at room temperature for 18 hours. DMF was removed, the residue was dissolved in CH$_2$Cl$_2$, and DCUrea was separated by filtration. The residue was washed successively with diluted hydrochloric acid, a saturated sodium hydrogen carbonate aqueous solution and a saturated saline solution, and then dried over anhydrous sodium sulfate. After the solvent was removed, the residue was purified by silica gel column chromatography using MeOH-CH$_2$Cl$_2$ to obtain the title compound.

Yield: 370 mg; Rf$_1$: 0.58, Rf$_2$: 0.38; [α]$_D$: −7.28 (C=1.15, DMF) FAB mass spectrum (M+1): 749 NMR (δ, DMSO-d$_6$, 55° C.): 1.35 (9H, s), 1.93 to 2.04 (2H, m), 2.90 (3H, s), 2.95 to 3.10 (6H, m), 3.40 (2H, t, J=6 Hz), 4.06 to 4.15 (2H, m), 4.36 to 4.40 (1H, m), 4.46 (2H, s), 4.58 (1H, d, J=15 Hz), 6.07 (1H, br), 6.84 (1H, br), 6.94 to 7.53 (15H, m), 8.16 (1H, br s), 10.02 (1H, br s), 10.75 (1H, br s)

Example 10
Boc-Asn-Trp-AzPhe-NH(CH$_2$)$_2$OCH$_2$Ph

In the same manner as in Example 2 (2), the title compound was obtained from 500 mg of Boc-Trp-AzPhe-NH(CH$_2$)$_2$OCH$_2$Ph, 2.50 ml of 4N HCl-AcOEt, 0.12 ml of Et3N, 0.09 ml of NMM and 300 mg of Boc-Asn-ONp.

Yield: 290 mg; Rf$_1$: 0.49, Rf$_2$: 0.24; [α]$_D$: −21.26 (C=1.20, DMF) FAB mass spectrum (M+1): 700 NMR (δ, DMSO-d$_6$, 55° C.): 1.33 (9H, s), 2.30 to 2.44 (2H, m), 2.96 to 3.11 (4H, m), 3.40 (2H, t, J=6 Hz), 4.21 to 4.39 (3H, m), 4.46 (2H, s), 4.52 (1H, d, J=15 Hz), 6.08 (1H, br), 6.67 (1H, br), 6.74 (1H, br), 6.93 to 7.52 (16H, m), 8.02 (1H, br s), 9.91 (1H, br s), 10.71 (1H, br s)

Example 11
Boc-Met-Trp-AzPhe-NH(CH$_2$)$_2$OCH$_2$Ph

In the same manner as in Example 2 (2), the title compound was obtained from 500 mg of Boc-Trp-AzPhe-NH(CH$_2$)$_2$OCH$_2$Ph, 2.00 ml of 4N HCl-AcOEt, 0.12 ml of Et$_3$N, 0.09 ml of NMM and 295 mg of Boc-Met-OSu.

Yield: 500 mg; Rf$_1$: 0.73, Rf$_2$: 0.58; [α]$_D$: −12.85 (C=1.04, DMF) NMR (δ, DMSO-d$_6$, 55° C.): 1.35 (9H, s), 1.73 to 1.83 (2H, m), 2.00 (3H, s), 2.40 (2H, t, J=7 Hz), 2.96 to 3.16 (4H, m), 3.40 (2H, t, J=6 Hz), 4.00 to 4.14 (2H, m), 4.35 to 4.42 (1H, m), 4.47 (2H, s), 4.59 (1H, d, J=14 Hz), 6.10 (1H, br), 6.72 (1H, br), 6.96 to 7.53 (15H, m), 8.07 (1H, br s), 9.96 (1H, br s), 10.74 (1H, br s)

Example 12
Z-Asn-Trp-AzPhe-NH(CH$_2$)$_2$OCH$_2$Ph

In the same manner as in Example 2 (2), the title compound was obtained from 450 mg of Boc-Trp-AzPhe-NH(CH$_2$)$_2$OCH$_2$Ph, 2.00 ml of 4N HCl-AcOEt, 0.11 ml of Et$_3$N, 0.09 ml of NMM and 272 mg of Z-Asn-ONp.

Yield: 290 mg; Rf$_1$: 0.53, Rf$_2$: 0.21; [α]$_D$: −20.27 (C=1.02, DMF) NMR (δ, DMSO-d$_6$, 55° C.): 2.40 (1H, dd, J=15 Hz, 8 Hz), 2.51 (1H, dd, J=15 Hz, 6 Hz), 2.93 to 3.21 (4H, m), 3.40 (2H, t, J=6 Hz), 4.22 to 4.40 (3H, m), 4.45 (2H, s), 4.53 (1H, d, J=15 Hz), 4.95 (1H, d, J=13 Hz), 5.01 (1H, d, J=13 Hz), 6.09 (1H, br), 6.75 (1H, br), 6.93 to 7.52 (22H, m), 8.12 (1H, br s), 9.92 (1H, br s), 10.72 (1H, br s)

Example 13
Boc-Orn-Trp-AzPhe-NH(CH$_2$)$_2$OCH$_2$Ph (1) Boc-Orn(Z)-Trp-AzPhe-NH(CH$_2$)$_2$OCH$_2$Ph In the same manner as in Example 2 (2), the title compound was obtained from 500 mg of Boc-Trp-AzPhe-NH(CH$_2$)$_2$OCH$_2$Ph, 2.50 ml of 4N HCl-AcOEt, 0.12 ml of Et$_3$N, 0.09 ml of NMM and 395 mg of Boc-Orn(Z)-OSu.

Yield: 570 mg; Rf$_1$: 0.72, Rf$_2$: 0.53; [α]$_D$: −14.17 (C=1.08, DMF) NMR (δ, DMSO-d$_6$, 55° C.): 1.34 to 1.55 (13H, m), 2.95 to 3.18 (6H, m), 3.38 (2H, t, J=6 Hz), 3.87 to 3.93 (1H, m), 4.12 (1H, d, J=14 Hz), 4.34 to 4.41 (1H, m), 4.45 (2H, s), 4.56 (1H, d, J=14 Hz), 5.01 (2H, s), 6.06 (1H, br), 6.60 (1H, br), 6.93 to 7.53 (21H, m), 8.01 (1H, br s), 9.93 (1H, br s), 10.72 (1H, br s)

(2) Boc-Orn-Trp-AzPhe-NH(CH$_2$)$_2$OCH$_2$Ph

In 15 ml of MeOH, 410 mg of Boc-Orn(Z)-Trp-AzPhe-NH(CH$_2$)$_2$OCH$_2$Ph was stirred in the presence of 41 mg of 10% palladium carbon for 18 hours in a hydrogen stream. After palladium carbon was separated by filtration, the solvent was removed. The residue was purified by silica gel column chromatography using MeOH-CH$_2$Cl$_2$ to obtain the title compound.

Yield: 170 mg; Rf$_1$: 0.18, Rf$_2$: 0.01; [α]$_D$: −23.09 (C=1.07, DMF) NMR (δ, DMSO-d$_6$, 55° C.) : 1.24 to 1.57 (13H, m), 2.89 to 3.17 (8H, m), 3.39 (2H, t, J=6 Hz), 3.87 to 3.94 (1H, m), 4.11 (1H, d, J=15 Hz), 4.35 to 4.40 (1H, m), 4.46 (2H, s), 4.58 (1H, d, J=15 Hz), 6.11 (1H, br), 6.62 (1H, br), 6.93 to 7.52 (16H, m), 8.08 (1H, br), 10.74 (1H, br s)

Example 14
Boc-Cit-Trp-AzPhe-NH(CH$_2$)$_2$OCH$_2$Ph

In the same manner as in Example 9, the title compound was obtained from 500 mg of Boc-Trp-AzPhe-NH(CH$_2$)$_2$OCH$_2$Ph, 2.50 ml of 4N HCl-AcOEt, 0.12 ml of Et$_3$N, 0.09 ml of NMM, 234 mg of Boc-Cit-OH, 176 mg of DCC and 115 mg of HOBt.

Yield: 410 mg; Rf$_1$: 0.47, Rf$_2$: 0.11; [α]$_D$: −19.82 (C=1.05, DMF) NMR (δ, DMSO-d$_6$, 55° C.): 1.28 to 1.61 (13H, m), 2.89 to 3.15 (6H, m), 3.39 (2H, t, J=6 Hz), 3.89 to 3.97 (1H, m), 4.11 (1H, d, J=15 Hz), 4.33 to 4.40 (1H, m), 4.46 (2H, s), 4.57 (1H, d, J=15 Hz), 5.24 (2H, br s), 5.80 (1H, br s), 6.10 (1H, br), 6.60 (1H, br), 6.93 to 7.53 (15H, m), 8.04 (1H, br s), 9.94 (1H, br s), 10.72 (1H, br s)

Example 15
Boc-Arg(NO$_2$)-Trp-AzPhe-NH(CH$_2$)$_2$OCH$_2$Ph (a guanidino group is substituted by NO$_2$)

In the same manner as in Example 2 (1), the title compound was obtained from 500 mg of Boc-Trp-AzPhe-NH ($CH_2$)$_2$O$CH_2$Ph, 2.50 ml of 4N HCl-AcOEt, 0.12 ml of $Et_3$N and Boc-Arg($NO_2$)-OH mixed acid anhydride (obtained by dissolving 272 mg of Boc-Arg($NO_2$)-OH in 5 ml of THF, adding 0.09 ml of N-methylmorpholine and 0.11 ml of isobutyl chloroformate to the solution under ice cooling and stirring the mixture for 1 hour).

Yield: 340 mg; $Rf_1$: 0.51, $Rf_2$: 0.18; $[\alpha]_D$: −17.44 (C=1.04, DMF) NMR (δ, DMSO-$d_6$, 55° C.): 1.35 (9H, s), 1.42 to 1.60 (4H, m), 2.95 to 3.16 (6H, m), 3.39 (2H, t, J=6 Hz), 3.90 to 3.98 (1H, m), 4.11 (1H, d, J=14 Hz), 4.35 to 4.42 (1H, m), 4.46 (2H, s), 4.57 (1H, d, J=14 Hz), 6.09 (1H, br), 6.67 (1H, br), 6.94 to 7.53 (16H, m), 7.78 (2H, br s), 8.06 (1H, br s), 9.95 (1H, br s), 10.72 (1H, br s)

Example 16
Boc-Asp-Trp-AzPhe-NH($CH_2$)$_2$O$CH_2$Ph (1) Boc-Asp(OBzl)-Trp-AzPhe-NH($CH_2$)$_2$O$CH_2$Ph In the same manner as in Example 2 (2), the title compound was obtained from 500 mg of Boc-Trp-AzPhe-NH($CH_2$)$_2$O$CH_2$Ph, 2.50 ml of 4N HCl-AcOEt, 0.12 ml of $Et_3$N, 0.09 ml of NMM and 385 mg of Boc-Asp(OBzl)-OSu.

Yield: 410 mg; $Rf_1$: 0.76, $Rf_2$: 0.65; $[\alpha]_D$: −28.67 (C=1.02, DMF) NMR (δ, DMSO-$d_6$, 55° C.): 1.34 (9H, s), 2.57 (1H, dd, J=16 Hz, 9 Hz), 2.71 (1H, dd, J=16 Hz, 5 Hz), 2.95 to 3.16 (4H, m), 3.38 (2H, t, J=6 Hz), 4.13 to 4.24 (1H, m), 4.34 to 4.38 (2H, m), 4.44 (2H, s), 4.51 to 4.57 (1H, m), 5.07 (2H, s), 6.05 (1H, br), 6.93 to 7.52 (21H, m), 8.01 (1H, br), 9.92 (1H, br s), 10.74 (1H, br s)

(2) Boc-Asp-Trp-AzPhe-NH($CH_2$)$_2$O$CH_2$Ph

In the same manner as in Example 13 (2), the title compound was obtained from 440 mg of Boc-Asp(OBzl)-Trp-AzPhe-NH($CH_2$)$_2$O$CH_2$Ph and 44 mg of 10% palladium carbon.

Yield: 170 mg; $Rf_1$: 0.48, $Rf_2$: 0.09; $[\alpha]_D$: −28.42 (C=1.09, DMF) NMR (δ, DMSO-$d_6$, 55° C.): 1.34 (9H, s), 2.44 (1H, dd, J=16 Hz, 8 Hz), 2.58 (1H, dd, J=16 Hz, 5 Hz), 2.89 to 3.20 (4H, m), 3.40 (2H, t, J=6 Hz), 4.16 to 4.37 (3H, m), 4.46 (2H, s), 4.55 (1H, d, J=14 Hz), 6.07 (1H, br), 6.82 to 7.52 (17H, m), 7.98 (1H, br s), 9.93 (1H, br s), 10.73 (1H, br s)

Example 17
Boc-Asp(OBzl)-Gln-Trp-AzPhe-NH$CH_2$Ph(4-F) ($CH_2$Ph(4-F): 4-fluorobenzyl)

(1) Boc-Trp-AzPhe-NH$CH_2$Ph(4-F)

In the same manner as in Example 2 (1), the title compound was obtained from 700 mg of Boc-AzPhe-NH$CH_2$Ph(4-F), 4.50 ml of 4N HCl-AcOEt, 0.26 ml of $Et_3$N and Boc-Trp-OH mixed acid anhydride (obtained by dissolving 636 mg of Boc-Trp-OH in 10 ml of THF, adding 0.21 ml of NMM and 0.24 ml of isobutyl chloroformate to the solution under ice cooling and stirring the mixture for 1 hour).

Yield: 630 mg; $Rf_3$: 0.24, $Rf_4$: 0.29; $[\alpha]_D$: −5.31 (C=1.04, DMF) NMR (δ, DMSO-$d_6$, 55° C.): 1.24 (9H, s), 2.89 to 3.04 (2H, m), 4.04 to 4.25 (4H, m), 4.67 (1H, d, J=15 Hz), 6.72 to 7.52 (16H, m), 10.06 (1H, br s), 10.71 (1H, br s)

(2) Boc-Gln-Trp-AzPhe-NH$CH_2$Ph(4-F)

In the same manner as in Example 2 (2), the title compound was obtained from 500 mg of Boc-Trp-AzPhe-NH$CH_2$Ph(4-F), 2.50 ml of 4N HCl-AcOEt, 0.13 ml of $Et_3$N, 0.10 ml of NMM and 327 mg of Boc-Gln-ONp.

Yield: 460 mg; $Rf_1$: 0.49, $Rf_2$: 0.21; $[\alpha]_D$: −13.59 (C=1.15, DMF) NMR (δ, DMSO-$d_6$, 55° C.): 1.34 (9H, s), 1.61 to 1.85 (2H, m), 2.05 to 2.12 (2H, m), 2.99 (1H, dd, J=15 Hz, 7 Hz), 3.09 (1H, dd, J=15 Hz, 7 Hz), 3.89 to 3.96 (1H, m), 4.00 to 4.16 (3H, m), 4.33 to 4.39 (1H, m), 4.62 (1H, d, J=15 Hz), 6.65 (2H, br), 6.93 to 7.25 (16H, m), 8.13 (1H, br s), 10.00 (1H, br s), 10.73 (1H, br s)

(3) Boc-Asp(OBzl)-Gln-Trp-AzPhe-NH$CH_2$Ph(4-F)

In the same manner as in Example 2 (2), the title compound was obtained from 160 mg of Boc-Gln-Trp-AzPhe-NH$CH_2$Ph(4-F), 0.50 ml of 4N HCl-AcOEt, 0.03 ml of $Et_3$N, 0.03 ml of NMM and 100 mg of Boc-Asp(OBzl)-OSu.

Yield: 190 mg; $Rf_1$: 0.52, $Rf_2$: 0.21; $[\alpha]_D$: −14.97 (C=0.98, DMF) NMR (δ, DMSO-$d_6$, 55° C.): 1.34 (9H, s), 1.66 to 1.86 (2H, m), 2.07 to 2.12 (2H, m), 2.59 (1H, dd, J=16 Hz, 9 Hz), 2.77 (1H, dd, J=16 Hz, 5 Hz), 2.95 to 3.15 (2H, m), 3.99 to 4.15 (3H, m), 4.24 to 4.34 (3H, m), 4.59 (1H, d, J=15 Hz), 5.07 (2H, s), 6.65 (2H, br), 6.92 to 7.51 (21H, m), 7.71 (1H, br s), 8.27 (1H, br s), 10.01 (1H, br s), 10.71 (1H, br s)

Example 18
Boc-Gln-Trp-AzPhe-NH($CH_2$)$_2$O$CH_2$Ph(4-F)

(1) Boc-Trp-AzPhe-NH($CH_2$)$_2$O$CH_2$Ph(4-F)

In the same manner as in Example 2 (1), the title compound was obtained from 2.00 g of Boc-AzPhe-NH($CH_2$)$_2$O$CH_2$Ph(4-F), 6.00 ml of 4N HCl-AcOEt, 0.67 ml of $Et_3$N and Boc-Trp-OH mixed acid anhydride (obtained by dissolving 1.62 g of Boc-Trp-OH in 15 ml of THF, adding 0.52 ml of NMM and 0.62 ml of isobutyl chloroformate to the solution under ice cooling and stirring the mixture for 1 hour).

Yield: 1.02 g; $Rf_3$: 0.20, $Rf_4$: 0.23; $[\alpha]_D$: −7.06 (C=1.38, DMF) NMR (δ, CDCl$_3$, 55° C.): 1.39 (9H, s), 3.14 (2H, d, J=7 Hz), 3.23 to 3.41 (2H, m), 3.52 (2H, t, J=5 Hz), 4.18 to 4.25 (1H, m), 4.46 to 4.52 (3H, s), 4.68 (1H, d, J=15 Hz), 4.92 (1H, d, J=6 Hz), 5.41 (1H, br), 6.90 to 7.59 (15H, m), 8.10 (1H, m)

(2) Boc-Gln-Trp-AzPhe-NH($CH_2$)$_2$O$CH_2$Ph(4-F)

In the same manner as in Example 2 (2), the title compound was obtained from 810 mg of Boc-Trp-AzPhe-NH($CH_2$)$_2$O$CH_2$Ph(4-F), 4.00 ml of 4N HCl-AcOEt, 0.19 ml of $Et_3$N, 0.15 ml of NMM and 493 mg of Boc-Gln-ONp.

Yield: 600 mg; $Rf_1$: 0.50, $Rf_2$: 0.18; $[\alpha]_D$: −20.28 (C=1.08, DMF) NMR (δ, DMSO-$d_6$, 55° C.): 1.34 (9H, s), 1.64 to 1.88 (2H, m), 1.98 to 2.16 (2H, m), 2.95 to 3.15 (4H, m), 3.38 (2H, t, J=6 Hz), 3.90 to 3.96 (1H, m), 4.11 (1H, d, J=15 Hz), 4.34 to 4.41 (1H, m), 4.44 (2H, s), 4.57 (1H, d, J=15 Hz), 6.09 (1H, br), 6.62 (1H, br), 6.94 to 7.53 (15H, m), 8.07 (1H, br s), 9.96 (1H, br s), 10.73 (1H, br s)

Example 19
Boc-Asp (OBzl)-Gln-Trp-AzPhe-NH($CH_2$)$_2$Ph (1) Boc-Trp-AzPhe-NH($CH_2$)$_2$Ph In the same manner as in Example 2 (1), the title compound was obtained from 1.00 g of Boc-AzPhe-NH($CH_2$)$_2$Ph, 6.00 ml of 4N HCl-AcOEt, 0.38 ml of $Et_3$N and Boc-Trp-OH mixed acid anhydride (obtained by dissolving 917 mg of Boc-Trp-OH in 10 ml of THF, adding 0.30 ml of NMM and 0.35 ml of isobutyl chloroformate to the solution under ice cooling and stirring the mixture for 1 hour).

Yield: 810 mg; $Rf_3$: 0.23, $Rf_4$: 0.30; $[\alpha]_D$: +8.83 (C=1.35, DMF) NMR (δ, CDCl$_3$, 55° C.): 1.40 (9H, s), 2.71 to 2.78 (2H, m), 3.11 to 3.14 (2H, m), 3.27 to 3.38 (2H, m), 4.13 to 4.20 (1H, m), 4.42 (1H, d, J=15 Hz), 4.73 (1H, d, J=15 Hz), 4.92 (1H, d, J=6 Hz), 5.45 (1H, br), 6.84 to 7.58 (16H, m), 7.82 (1H, m)

(2) Boc-Gln-Trp-AzPhe-NH($CH_2$)$_2$Ph

In the same manner as in Example 2 (2), the title compound was obtained from 630 mg of Boc-Trp-AzPhe-NH($CH_2$)$_2$Ph, 3.00 ml of 4N HCl-AcOEt, 0.16 ml of $Et_3$N, 0.13 ml of NMM and 415 mg of Boc-Gln-ONp.

Yield: 420 mg; $Rf_1$: 0.48, $Rf_2$: 0.14; $[\alpha]_D$: −10.00 (C=1.12, DMF) NMR (δ, CDCl$_3$, 55° C.): 1.31 (9H, s), 1.85 to 1.91 (2H, m), 2.17 (2H, t, J=6 Hz), 2.76 (2H, t, J=7 Hz), 3.18 (2H, d, J=7 Hz), 3.35 (2H, t, J=7 Hz), 3.95 to 3.99 (1H, m), 4.38 to 4.49 (2H, m), 4.70 (1H, d, J=15 Hz), 5.60 (3H, br), 6.89 to 7.54 (17H, m), 7.96 (1H, br s), 8.21 (1H, br)
(3) Boc-Asp(OBzl)-Gln-Trp-AzPhe-NH(CH$_2$)$_2$Ph

In the same manner as in Example 2 (2), the title compound was obtained from 250 mg of Boc-Gln-Trp-AzPhe-NH(CH$_2$)$_2$Ph, 1.00 ml of 4N HCl-AcOEt, 0.05 ml of Et$_3$N, 0.04 ml of NMM and 154 mg of Boc-Asp(OBzl)-OSu.

Yield: 200 mg; Rf$_1$: 0.53, Rf$_2$: 0.24; [α]$_D$: −10.60 (C=1.09, DMF) NMR (δ, DMSO-d$_6$, 55° C.): 1.35 (9H, s), 1.70 to 1.98 (2H, m), 2.13 (2H, t, J=8 Hz), 2.57 to 2.65 (3H, m), 2.79 (1H, dd, J=16 Hz, 5 Hz), 2.95 to 3.15 (4H, m), 4.08 (1H, br), 4.27 to 4.39 (3H, m), 4.56 (1H, d, J=15 Hz), 5.06 (5H, s), 6.07 (1H, br), 6.61 (1H, br), 6.94 to 7.53 (22H, m), 7.80 (1H, br s), 8.26 (1H, br s), 9.95 (1H, br s), 10.75 (1H, br s)

Example 20
Boc-Asp(OBzl)-Gln-Trp-AzPhe-NHCH$_2$Ph
(1) Boc-Trp-AzPhe-NHCH$_2$Ph

In the same manner as in Example 1 (1), the title compound was obtained from 1.50 g of Boc-AzPhe-NHCH$_2$Ph, 803 mg of 4-toluenesulfonic acid monohydrate and Boc-Trp-OH mixed acid anhydride (obtained by dissolving 1.43 g of Boc-Trp-OH in 20 ml of THF, adding 0.47 ml of NMM and 0.55 ml of isobutyl chloroformate to the solution under ice cooling and stirring the mixture for 1 hour).

Yield: 600 mg; Rf$_3$: 0.23, Rf$_4$: 0.29; [α]$_D$: −5.13 (C=0.55, DMF) NMR (δ, CDCl$_3$, 55° C.): 1.31 (9H, s), 3.11 to 3.15 (2H, m), 4.16 to 4.23 (1H, m), 4.29 to 4.35 (2H, m), 4.49 (1H, d, J=15 Hz), 4.74 (1H, d, J=l5 Hz), 4.91 (1H, d, J=6 Hz), 5.70 (1H, br), 6.82 to 7.56 (17H, m)
(2) Boc-Gln-Trp-AzPhe-NHCH$_2$Ph In the same manner as in Example 2 (2), the title compound was obtained from 470 mg of Boc-Trp-AzPhe-NHCH$_2$Ph, 2.20 ml of 4N HCl-AcOEt, 0.12 ml of Et$_3$N, 0.10 ml of NMM and 320 mg of Boc-Gln-ONp.

Yield: 540 mg; Rf$_1$: 0.47, Rf$_2$: 0.13; [α]$_D$: −14.45 (C=0.70, DMF) NMR (δ, CDCl$_3$, 55° C.): 1.30 (9H, s), 1.37 to 1.80 (2H, m), 2.10 to 2.15 (2H, m), 3.18 (2H, d, J=7 Hz), 3.89 to 3.95 (1H, m), 4.24 to 4.45 (4H, m), 4.81 (1H, d, J=14 Hz), 5.38 (1H, br), 6.86 to 7.53 (16H, m), 7.85 (2H, br)
(3) Boc-Asp(OBzl)-Gln-Trp-AzPhe-NHCH$_2$Ph In the same manner as in Example 2 (2), the title compound was obtained from 470 mg of Boc-Gln-Trp-AzPhe-NHCH$_2$Ph, 2.00 ml of 4N HCl-AcOEt, 0.10 ml of Et$_3$N, 0.08 ml of NMM and 295 mg of Boc-Asp(OBzl)-OSu.

Yield: 590 mg; Rf$_1$: 0.52, Rf$_2$: 0.26; [α]$_D$: −17.21 (C=1.13, DMF) NMR (δ, CDCl$_3$, 55° C.): 1.43 (9H, s), 1.75 to 1.83 (2H, m), 1.98 to 2.04 (2H, m), 2.60 (1H, dd, J=17 Hz, 6 Hz), 2.70 (1H, dd, J=17 Hz, 5 Hz), 3.15 (1H, dd, J=15 Hz, 8 Hz), 3.27 (1H, dd, J=15 Hz, 6 Hz), 3.98 to 4.06 (1H, m), 4.13 to 4.19 (1H, m), 4.32 (1H, d, J=15 Hz), 4.44 (1H, d, J=15 Hz), 4.45 to 4.52 (1H, m), 4.60 to 4.72 (2H, m), 5.02 (2H, s), 5.28 to 5.70 (3H, br m), 6.89 to 7.53 (22H, m), 7.92 (1H, br s), 8.13 (1H, br s), 8.20 (1H, br)

Example 21
i-Pent-CO-Asp(OBzl)-Gln-Trp-AzPhe-NHCH$_2$Ph (i-Pent: isopentyl)

In the same manner as in Example 2 (2), the title compound was obtained from 280 mg of Boc-Asp(OBzl)-Gln-Trp-AzPhe-NHCH$_2$Ph, 1.00 ml of 4N HCl-AcOEt, 0.05 ml of Et$_3$N, 0.04 ml of NMM and 68 mg of 4-methylvaleric acid N-hydroxysuccinimide ester.

Yield: 170 mg; Rf$_1$: 0.53, Rf$_2$: 0.22; [α]$_D$: −20.17 (C=1.01, DMF) NMR (δ, DMSO-d$_6$, 55° C.): 0.81 (6H, d, J=6 Hz), 1.32 to 1.52 (3H, m), 1.65 to 1.86 (2H, m), 2.05 to 2.12 (4H, m), 2.60 (1H, dd, J=16 Hz, 9 Hz), 2.79 (1H, dd, J=16 Hz, 6 Hz), 2.95 to 3.15 (2H, m), 4.02 to 4.38 (5H, m), 4.55 to 4.65 (2H, m), 5.07 (2H, s), 6.65 (2H, br), 6.92 to 7.51 (21H, m), 7.79 (1H, d, J=7 Hz), 8.02 (1H, br s), 8.18 (1H, br s), 9.99 (1H, br s), 10.71 (1H, br s)

Example 22
Boc-Asp(OBzl)-Gln-Trp-AzPhe-NHDmob

In the same manner as in Example 2 (2), the title compound was obtained from 1.00 g of Boc-Gln-Trp-AzPhe-NHDmob of Example 1 (2), 4.00 ml of 4N HCl-AcOEt, 0.22 ml of Et$_3$N, 0.17 ml of NMM and 670 mg of Boc-Asp(OBzl)-OSu.

Yield: 1.15 g; Rf$_1$: 0.52, Rf$_2$: 0.22; [α]$_D$: −20.20 (C=1.16, DMF) NMR (δ, DMSO-d6, 55° C.): 1.36 (9H, s), 1.69 to 1.90 (2H, m), 2.08 (2H, t, J=8 Hz), 2.61 (1H, dd, J=16 Hz, 8 Hz), 2.77 (1H, dd, J=16 Hz, 5 Hz), 2.91 to 3.15 (2H, m), 3.71 (3H, s), 3.78 (3H, s), 3.81 to 3.98 (3H, m), 4.25 to 4.37 (3H, m), 4.59 (1H, d, J=15 Hz), 5.07 (2H, s), 5.68 (2H, br s), 6.36 to 6.62 (3H, m), 6.75 to 7.47 (17H, m), 7.74 (1H, d, J=7 Hz), 8.20 (1H, br s), 9.82 (1H, br s), 10.41 (1H, br s)

Example 23
Boc-Asp(OBzl)-Gln-Trp-AzPhe-NHCH$_3$
(1) Boc-Trp-AzPhe-NHCH$_3$

In the same manner as in Example 1 (1), the title compound was obtained from 460 mg of Boc-AzPhe-NHCH$_3$, 330 mg of 4-toluenesulfonic acid monohydrate and Boc-Trp-OH mixed acid anhydride (obtained by dissolving 560 mg of Boc-Trp-OH in 5 ml of THF, adding 0.18 ml of NMM and 0.21 ml of isobutyl chloroformate to the solution under ice cooling and stirring the mixture for 1 hour).

Yield: 200 mg; Rf$_3$: 0.10, Rf$_4$: 0.12; [α]$_D$: −12.30 (C=0.86, DMF) NMR (δ, CDCl$_3$, 55° C.): 1.41 (9H, s), 2.65 (3H, s), 3.07 to 3.22 (2H, m), 4.13 to 4.21 (1H, m), 4.38 (1H, d, J=15 Hz), 4.75 (1H, d, J=15 Hz), 4.98 (1H, d, J=6 Hz), 5.40 (1H, br), 6.95 to 7.59 (11H, m), 8.03 (1H, br)
(2) Boc-Gln-Trp-AzPhe-NHCH$_3$ In the same manner as in Example 2 (2), the title compound was obtained from 530 mg of Boc-Trp-AzPhe-NHCH3, 3.00 ml of 4N HCl-AcOEt, 0.16 ml of Et3N, 0.13 ml of NMM and 419 mg of Boc-Gln-ONp.

Yield: 590 mg; Rf$_1$: 0.38, Rf$_2$: 0.06; [α]$_D$: −29.50 (C=1.10, DMF) NMR (δ, CDCl$_3$, 55° C.): 1.30 (9H, s), 1.92 (2H, td, J=6 Hz, 6 Hz), 2.20 (2H, t, J=6 Hz), 2.65 (3H, s), 3.21 (2H, d, J=7 Hz), 3.99 to 4.05 (1H, m), 4.42 to 4.49 (2H, m), 4.74 (1H, d, J=15 Hz), 5.65 (3H, br), 6.97 to 7.56 (12H, m), 8.00 (1H, br s), 8.29 (1H, br s)
(3) Boc-Asp(OBzl)-Gln-Trp-AzPhe-NHCH$_3$ In the same manner as in Example 2 (2), the title compound was obtained from 500 mg of Boc-Gln-Trp-AzPhe-NHCH$_3$, 2.00 ml of 4N HCl-AcOEt, 0.12 ml of Et3N, 0.09 ml of NMM and 355 mg of Boc-Asp(OBzl)-OSu.

Yield: 550 mg; Rf$_1$: 0.49, Rf$_2$: 0.14; [α]$_D$: −30.00 (C=1.01, DMF) NMR (δ, DMSO-d$_6$, 55° C.): 1.37 (9H, s), 1.71 to 1.91 (2H, m), 2.10 (2H, t, J=7 Hz), 2.49 (3H, s), 2.61 (1H, dd, J=16 Hz, 9 Hz), 2.79 (1H, dd, J=16 Hz, 5 Hz), 2.98 (1H, dd, J=15 Hz, 7 Hz), 3.09 (1H, dd, J=15 Hz, 8 Hz), 4.02 to 4.09 (1H, m), 4.27 to 4.33 (3H, m), 4.48 to 4.58 (1H, m), 5.08 (2H, s), 5.83 (1H, br), 6.60 (1H, br), 6.94 to 7.52 (17H, m), 7.76 (1H, br s), 8.29 (1H, br s), 9.90 (1H, br s), 10.75 (1H, br s)

Example 24
Boc-Asp(OBzl)-Gln-Trp-AzPhe-NH(CH$_2$)$_2$OH
(1) Boc-Gln-Trp-AzPhe-NH(CH$_2$)$_2$OH In 10 ml of 80% acetic acid, 200 mg of Boc-Gln-Trp-AzPhe-NH(CH$_2$)$_2$OCH$_2$Ph was stirred in the presence of 100 mg of 10% palladium carbon for 18 hours in a hydrogen stream. After palladium carbon was separated by filtration, the solvent was removed and the residue was dried under reduced pressure. The residue was purified by silica gel column chromatography using MeOH-CH$_2$Cl$_2$ to obtain the title compound.

Yield: 143 mg; Rf$_1$: 0.27, Rf$_2$: 0.07; [α]$_D$: −19.40 (C=1.2, DMF) NMR (δ, CD$_3$OD, 55° C.): 1.40 (9H, s), 1.82 to 2.05 (2H, m), 2.27 (2H, t, J=8 Hz), 3.13 to 3.25 (4H, m), 3.57 (2H, t, J=6 Hz), 3.90 (1H, d, J=15 Hz), 4.06 (1H, t, J=7 Hz), 4.38 (1H, t, J=8 Hz), 4.76 (1H, d, J=15 Hz), 6.38 (1H, br), 6.86 to 7.58 (10H, m)

(2) Boc-Asp(OBzl)-Gln-Trp-AzPhe-NH(CH$_2$)$_2$OH

In the same manner as in Example 2 (2), the title compound was obtained from 110 mg of Boc-Gln-Trp-AzPhe-NH(CH$_2$)$_2$OH, 0.50 ml of 4N HCl-AcOEt, 0.03 ml of Et$_3$N, 0.02 ml of NMM and 74 mg of Boc-Asp(OBzl)-OSu.

Yield: 70 mg; Rf$_1$: 0.43, Rf$_2$: 0.09; [α]$_D$: −21.30 (C=0.90, DMF) NMR (δ, DMSO-d$_6$, 55° C.): 1.37 (9H, s), 1.68 to 1.94 (2H, m), 2.10 (2H, t, J=6 Hz), 2.60 (2H, dd, J=16 Hz, 9 Hz), 2.79 (2H, dd, J=16 Hz, 5 Hz), 2.93 to 3.11 (4H, m), 3.36 (2H, td, J=6 Hz, 6 Hz), 4.08 (1H, d, J=15 Hz), 4.25 to 4.35 (3H, m), 4.56 (1H, d, J=15 Hz), 5.08 (2H, s), 6.03 (1H, br), 6.61 (1H, br), 6.91 to 7.52 (18H, m), 7.75 (1H, d, J=8 Hz), 8.24 (1H, br s), 9.93 (1H, br s), 10.70 (1H, br s)

Example 25
Boc-Asp(OBzl)-Gln-Trp-AzPhe-NHCH$_2$CH(CH$_3$)$_2$
(1) Boc-Trp-AzPhe-NHCH$_2$CH(CH$_3$)$_2$ In the same manner as in Example 1 (1), the title compound was obtained from 1.13 g of Boc-AzPhe-NHCH$_2$CH(CH$_3$)$_2$, 670 mg of 4-toluenesulfonic acid monohydrate and Boc-Trp-OH mixed acid anhydride (obtained by dissolving 1.19 g of Boc-Trp-OH in 10 ml of THF, adding 0.39 ml of NMM and 0.46 ml of isobutyl chloroformate to the solution under ice cooling and stirring the mixture for 1 hour).

Yield: 460 mg; Rf$_3$: 0.20, Rf$_4$: 0.27; [α]$_D$: −0.55 (C=1.28, DMF) NMR (δ, CDCl$_3$, 55° C.): 0.85 (6H, d, J=7 Hz), 1.39 (9H, s), 1.65 to 1.76 (1H, m), 2.96 to 3.24 (4H, m), 4.13 to 4.22 (1H, m), 4.37 (1H, d, J=15 Hz), 4.76 (1H, d, J=15 Hz), 4.91 (1H, d, J=6 Hz), 5.61 (1H, br), 6.95 to 7.59 (11H, m), 7.94 (1H, br)

(2) Boc-Gln-Trp-AzPhe-NHCH$_2$CH(CH$_3$)$_2$

In the same manner as in Example 2 (2), the title compound was obtained from 400 mg of Boc-Trp-AzPhe-NHCH$_2$CH(CH$_3$)$_2$, 2.00 ml of 4N HCl-AcOEt, 0.11 ml of Et$_3$N, 0.09 ml of NMM and 290 mg of Boc-Gln-ONp.

Yield: 400 mg; Rf$_1$: 0.44, Rf$_2$: 0.14; [α]$_D$: −22.60 (C=0.99, DMF) NMR (δ, CDCl$_3$, 55° C.): 0.87 (6H, d, J=7 Hz), 1.29 (9H, s), 1.68 to 1.80 (1H, m), 1.91 (2H, td, J=6 Hz, 6 Hz), 2.20 (2H, t, J=6 Hz), 2.98 (2H, t, J=6 Hz), 3.14 to 3.28 (2H, m), 3.95 to 4.01 (1H, m), 4.38 to 4.45 (1H, m), 4.51 (1H, d, J=15 Hz), 4.71 (1H, d, J=15 Hz), 5.40 (1H, br), 5.58 (1H, d, J=5 Hz), 5.74 (1H, br), 6.93 to 7.56 (12H, m), 7.97 (1H, br S), 8.14 (1H, br s)

(3) Boc-Asp(OBzl)-Gln-Trp-AzPhe-NHCH$_2$CH(CH$_3$)$_2$

In the same manner as in Example 2 (2), the title compound was obtained from 300 mg of Boc-Gln-Trp-AzPhe-NHCH$_2$-CH(CH$_3$)$_2$, 1.20 ml of 4N HCl-AcOEt, 0.07 ml of Et$_3$N, 0.05 ml of NMM and 198 mg of Boc-Asp(OBzl)-OSu.

Yield: 320 mg; Rf$_1$: 0.53, Rf$_2$: 0.21 [α]$_D$: −17.40 (C=0.53, DMF) NMR (δ, DMSO-d$_6$, 55° C.): 0.77 (6H, d, J=7 Hz), 1.37 (9H, s), 1.57 to 1.93 (3H, m), 2.08 to 2.14 (2H, m), 2.60 (1H, dd, J=16 Hz, 9 Hz), 2.75 to 2.82 (3H, m), 2.97 (1H, dd, J=15 Hz, 7 Hz), 3.07 (1H, dd, J=15 Hz, 8 Hz), 4.04 (1H, d, J=14 Hz), 4.25 to 4.38 (3H, m), 4.58 (1H, d, J=14 Hz), 5.08 (2H, s), 5.97 (1H, br), 6.60 (1H, br), 6.93 to 7.51 (17H, m), 7.70 (1H, d, J=8 Hz), 8.23 (1H, br), 9.92 (1H, br s), 10.72 (1H, br s)

Example 26
Boc-Asp(OBzl)-Gln-Trp-AzPhe-M
(1) Boc-Trp-AzPhe-M

In the same manner as in Example 1 (1), the title compound was obtained from 1.00 g of Boc-AzPhe-M, 567 mg of 4-toluenesulfonic acid monohydrate and Boc-Trp-OH mixed acid anhydride (obtained by dissolving 1.01 g of Boc-Trp-OH in 10 ml of THF, adding 0.33 ml of NMM and 0.39 ml of isobutyl chloroformate to the solution under ice cooling and stirring the mixture for 1 hour).

Yield: 960 mg; Rf$_3$: 0.10, Rf$_4$: 0.12; [α]$_D$: −20.50 (C=1.27, DMF) NMR (δ, CDCl$_3$, 55° C.): 1.38 (9H, s), 3.18 (2H, d, J=7 Hz), 3.27 (4H, t, J=5 Hz), 3.54 (4H, t, J=5 Hz), 4.30 to 4.46 (3H, m), 4.89 (1H, d, J=7 Hz), 6.96 to 7.63 (1H, m), 8.00 (1H, br s)

(2) Boc-Gln-Trp-AzPhe-M

In the same manner as in Example 2 (2), the title compound was obtained from 930 mg of Boc-Trp-AzPhe-M, 4.50 ml of 4N HCl-AcOEt, 0.25 ml of Et$_3$N, 0.20 ml of NMM and 655 mg of Boc-Gln-ONp.

Yield: 700 mg; Rf$_1$: 0.45, Rf$_2$: 0.09 [α]$_D$: −27.40 (C=1.06, DMF) NMR (δ, CDCl$_3$, 55° C.): 1.36 (9H, 3), 1.80 to 1.95 (2H, m), 2.11 to 2.17 (2H, m), 3.14 to 3.31 (4H, m), 3.56 (4H, t, J=5 Hz), 3.96 (1H, br), 4.36 (1H, d, J=15 Hz), 4.42 (1H, d, J=15 Hz), 4.66 to 4.73 (1H, m), 5.46 (3H, br), 6.76 to 7.61 (11H, m), 8.08 (1H, br), 8.17 (1H, br s)

(3) Boc-Asp(OBzl)-Gln-Trp-AzPhe-M

In the same manner as in Example 2 (2), the title compound was obtained from 500 mg of Boc-Gln-Trp-AzPhe-M, 2.00 ml of 4N HCl-AcOEt, 0.11 ml of Et$_3$N, 0.09 ml of NMM and 324 mg of Boc-Asp(OBzl)-OSu.

Yield: 500 mg; Rf$_1$: 0.52, Rf$_2$: 0.18; [α]$_D$: −21.80 (C=1.01, DMF) NMR (δ, DMSO-d$_6$, 55° C.): 1.36 (9H, s), 1.66 to 1.93 (2H, m), 2.08 (2H, t, J=8 Hz), 2.61 (1H, dd, J=16 Hz, 9 Hz), 2.78 (1H, dd, J=16 Hz, 5 Hz), 2.89 (1H, dd, J=15 Hz, 8 Hz), 3.02 (1H, dd, J=15 Hz, 6 Hz), 3.08 to 3.14 (4H, m), 3.41 (4H, t, J=5 Hz), 4.20 to 4.53 (5H, m), 5.08 (2H, s), 6.58 (1H, br), 6.93 to 7.54 (17H, m), 7.70 (1H, d, J=8 Hz), 8.12 (1H, br s), 10.10 (1H, br s), 10.67 (1H, br s)

Example 27
Boc-Asp(OBzl)-Gln-D-Trp-AzPhe-NH$_2$
(1) Z-D-Trp-AzPhe-NHDmob

In the same manner as in Example 1 (1), the title compound was obtained from 1.62 g of Boc-AzPhe-NHDmob, 742 mg of 4-toluenesulfonic acid monohydrate and Boc-D-Trp-OH mixed acid anhydride (obtained by dissolving 1.30 g of Boc-D-Trp-OH in 10 ml of THF, adding 0.83 ml of NMM and 0.50 ml of isobutyl chloroformate to the solution under ice cooling and stirring the mixture for 1 hour).

Yield: 1.00 g; Rf$_3$: 0.21, Rf$_4$: 0.22; [α]$_D$: +19.17 (C=1.48, DMF) NMR (δ, DMSO-d$_6$, 55° C.): 2.93 (1H, dd, J=14 Hz, 8 Hz), 3.03 (1H, dd, J=14 Hz, 6 Hz), 3.70 (3H, s), 3.74 (3H, s), 4.12 to 4.21 (4H, m), 4.66 (1H, d, J=14 Hz), 4.76 (1H, d, J=13 Hz), 4.83 (1H, d, J=13 Hz), 6.39 to 6.49 (3H, m), 6.92 to 7.54 (17H, m), 10.10 (1H, br s), 10.69 (1H, br s)

(2) Boc-Gln-D-Trp-AzPhe-NHDmob

In the same manner as in Example 1 (2), the title compound was obtained from 950 mg of Z-D-Trp-AzPhe-NHDmob, 95 mg of 10% palladium carbon, 0.16 ml of NMM and 549 mg of Boc-Gln-ONp.

Yield: 1.00 g; Rf$_1$: 0.45, Rf$_2$: 0.19; [α]$_D$: −11.42 (C=1.02, DMF) NMR (δ, DMSO-d$_6$, 55° C.): 1.32 (9H, s), 1.59 to 1.77 (2H, m), 1.99 (2H, t, J=7 Hz), 2.96 to 3.16 (2H, m), 3.73 (3H, s), 3.76 (3H, s), 3.86 to 3.92 (1H, m), 4.00 to 4.21 (3H, m), 4.31 to 4.40 (1H, m), 4.50 (1H, d, J=14 Hz), 6.36 to 6.73 (5H, m), 6.93 to 7.53 (12H, m), 8.07 (1H, br), 9.90 (1H, br s), 10.71 (1H, br s)

(3) Boc-Asp(OBzl)-Gln-D-Trp-AzPhe-NH$_2$

In the same manner as in Example 1 (3), the title compound was obtained from 300 mg of Boc-Gln-D-Trp-AzPhe-NHDmob, 3.60 ml of TFA-ethanedithiol-dimethyl sulfide (10:1:1), 0.06 ml of Et$_3$N, 172 mg of Boc-Asp(OBzl)-OSu and 0.05 ml of NMM.

Yield: 186 mg; Rf$_1$: 0.36, Rf$_2$: 0.07; [α]$_D$: +3.45 (C=1.30, DMF) NMR (δ, DMSO-d$_6$, 55° C.): 1.38 (9H, s), 1.68 to 1.88 (2H, m), 2.01 (2H, t, J=8 Hz), 2.61 (1H, dd, J=16 Hz, 9 Hz), 2.78 (1H, dd, J=16 Hz, 5 Hz), 2.91 to 3.14 (2H, m), 4.13 to 4.23 (1H, m), 4.29 to 4.39 (2H, m), 4.48 to 4.56 (2H, m), 5.09 (2H, s), 5.76 (2H, br s), 6.57 (1H, br), 6.91 to 7.53 (17H, m), 7.90 (1H, br), 8.11 (1H, br), 9.90 (1H, br s), 10.68 (1H, br s)

Example 28
Boc-Asp(OBzl)-Gln-Trp-AzPhe-OBzl
(1) Boc-Trp-AzPhe-OBzl

In the same manner as in Example 2 (1), the title compound was obtained from 1.02 g of Boc-AzPhe-OBzl, 7.00 ml of 4N HCl-AcOEt, 0.39 ml of Et$_3$N and Boc-Trp-OH mixed acid anhydride (obtained by dissolving 951 mg of Boc-Trp-OH in 10 ml of THF, adding 0.31 ml of NMM and 0.37 ml of isobutyl chloroformate to the solution under ice cooling and stirring the mixture for 1 hour).

Yield: 1.43 g; Rf$_3$: 0.40, Rf$_4$: 0.42; [α]$_D$: -2.78 (C=1.55, DMF) NMR (δ, CDCl$_3$, 55° C.): 1.34 (9H, s), 3.16 (2H, d, J=6 Hz), 4.37 to 4.43 (1H, m), 4.51 (1H, d, J=15 Hz), 4.70 (1H, d, J=15 Hz), 4.91 (1H, d, J=7 Hz), 5.12 (1H, d, J=12 Hz), 5.17 (1H, d, J=12 Hz), 6.89 to 7.60 (16H, m), 7.81 (1H, br)

(2) Boc-Gln-Trp-AzPhe-OBzl

In the same manner as in Example 2 (2), the title compound was obtained from 550 mg of Boc-Trp-AzPhe-OBzl, 2.50 ml of 4N HCl-AcOEt, 0.14 ml Et$_3$N, 0.11 ml of NMM and 371 mg of Boc-Gln-ONp.

Yield: 500 mg; Rf$_1$: 0.50, Rf$_2$: 0.19; [α]$_D$: -7.06 (C=1.41, DMF) NMR (δ, CDCl$_3$, 55° C.): 1.34 (9H, s), 1.79 to 1.90 (2H, m), 2.10 (2H, t, J=6 Hz), 3.19 to 3.23 (2H, m), 3.93 to 3.98 (1H, m), 4.46 (1H, d, J=15 Hz), 4.69 to 4.75 (2H, m), 5.12 (1H, d, J=12 Hz), 5.17 (1H, d, J=12 Hz), 6.95 to 7.57 (16H, m), 8.00 (1H, br), 8.35 (1H, br)

(3) Boc-Asp(OBzl)-Gln-Trp-AzPhe-OBzl

In the same manner as in Example 2 (2), the title compound was obtained from 300 mg of Boc-Gln-Trp-AzPhe-OBzl, 1.20 ml of 4N HCl-AcOEt, 0.06 ml of Et$_3$N, 0.05 ml of NMM and 188 mg of Boc-Asp(OBzl)-OSu.

Yield: 293 mg; Rf$_1$: 0.59, Rf$_2$: 0.31 [α]$_D$: -12.30 (C=1.4, DMF) NMR (δ, DMSO-d$_6$, 55° C.): 1.35 (9H, s), 1.64 to 1.92 (2H, m), 2.07 (2H, t, J=8 Hz), 2.60 (1H, dd, J=16 Hz, 9 Hz), 2.77 (1H, dd, J=16 Hz, 5 Hz), 2.87 (1H, dd, J=15 Hz, 8 Hz), 3.04 (1H, dd, J=15 Hz, 5 Hz), 4.24 to 4.58 (5H, m), 5.07 (2H, s), 5.09 (2H, s), 6.58 (1H, br), 6.91 to 7.51 (22H, m), 7.67 (1H, d, J=7 Hz), 8.04 (1H, br s), 10.31 (1H, br s), 10.62 (1H, br s)

Example 29
Boc-Asp(OBzl)-Gln-Trp-AzPhe-NHPh
(1) Boc-Trp-AzPhe-NHPh

In 10 ml of THF, 559 mg of Boc-Trp-AzPhe-OBzl was stirred in the presence of 60 mg of 10% palladium carbon for 18 hours in a hydrogen stream. After palladium carbon was separated by filtration, the solvent was removed. The residue was dried under reduced pressure and then dissolved in 10 ml of DMF. To the solution was added 0.11 ml of phenyl isocyanate, and the mixture was stirred at room temperature for 18 hours. After removing DMF, the residue was dissolved in AtOEt, washed successively with diluted hydrochloric acid, a saturated sodium hydrogen carbonate aqueous solution and a saturated saline solution, and then dried over anhydrous sodium sulfate. After the solvent was removed, the residue was purified by silica gel column chromatography using AcOEt-hexane to obtain the title compound.

Yield: 490 mg; Rf$_3$: 0.34, Rf$_4$: 0.44; [α]$_D$: -59.50 (C=1.09, DMF) NMR (δ, CDCl$_3$, 55° C.): 1.38 (9H, s), 3.11 (1H, dd, J=14 Hz, 7 Hz), 3.23 (1H, dd, J=14 Hz, 8 Hz), 4.18 to 4.25 (1H, m), 4.41 (1H, d, J=15 Hz), 4.85 (1H, d, J=15 Hz), 4.95 (1H, d, J=5 Hz), 6.97 to 7.65 (17H, m), 7.93 (1H, br s)

(2) Boc-Gln-Trp-AzPhe-NHPh

In the same manner as in Example 2 (2), the title compound was obtained from 410 mg of Boc-Trp-AzPhe-NHPh, 2.00 ml of 4N HCl-AcOEt, 0.11 ml of Et$_3$N, 0.09 ml of NMM and 287 mg of Boc-Gln-ONp.

Yield: 380 mg; Rf$_1$: 0.48, Rf$_2$: 0.14; [α]$_D$: +9.44 (C=1.05, DMF) NMR (δ, CDCl$_3$, 55° C.): 1.27 (9H, s), 1.83 to 1.90 (2H, m), 2.10 (2H, t, J=6 Hz), 3.15 to 3.30 (2H, m), 3.98 to 4.20 (1H, m), 4.38 to 4.52 (2H, m), 4.80 (1H, d, J=15 Hz), 5.45 (2H, br), 5.61 (1H, br), 6.94 to 7.58 (16H, m), 7.85 (1H, br), 8.20 (1H, br s), 8.33 (1H, br s)

(3) Boc-Asp(OBzl)-Gln-Trp-AzPhe-NHPh

In the same manner as in Example 2 (2), the title compound was obtained from 300 mg of Boc-Gln-Trp-AzPhe-NHPh, 1.20 ml of 4N HCl-AcOEt, 0.06 ml of Et$_3$N, 0.05 ml of NMM and 193 mg of Boc-Asp(OBzl)-OSu.

Yield: 370 mg; Rf$_1$: 0.52, Rf$_2$: 0.27; [α]$_D$: +14.62 (C=1.02, DMF) NMR (δ, DMSO-d$_6$, 55° C.): 1.36 (9H, s), 1.71 to 1.96 (2H, m), 2.09 to 2.16 (2H, m), 2.61 (1H, dd, J=16 Hz, 9 Hz), 2.80 (1H, dd, J=16 Hz, 5 Hz), 3.01 to 3.11 (2H, m), 3.79 to 3.94 (1H, m), 4.34 to 4.41 (3H, m), 4.73 (1H, d, J=14 Hz), 5.08 (2H, s), 6.62 (1H, br), 6.89 to 7.59 (22H, m), 7.86 (1H, br s), 8.26 (1H, br s), 8.42 (1H, br s), 10.24 (1H, br s), 10.77 (1H, br s)

Example 30
Boc-Gln-Trp-AzPhe(4-F)-NH(CH$_2$)$_2$OCH$_2$Ph
(1) Boc-Trp-AzPhe(4-F)-NH(CH$_2$)$_2$OCH$_2$Ph In the same manner as in Example 2 (1), the title compound was obtained from 800 mg of Boc-AzPhe(4-F)-NH(CH$_2$)$_2$OCH$_2$Ph, 5.00 ml of 4N HCl-AcOEt, 0.27 ml of Et$_3$N and Boc-Trp-OH mixed acid anhydride (obtained by dissolving 580 mg of Boc-Trp-OH in 10 ml of THF, adding 0.21 ml of NMM and 0.26 ml of isobutyl chloroformate to the solution under ice cooling and stirring the mixture for 1 hour).

Yield: 300 mg; Rf$_3$: 0.18, Rf$_4$: 0.20; [α]$_D$: -5.20 (C=1.10, DMF) NMR (δ, DMSO-d$_6$, 55° C.): 1.33 (9H, s), 2.89 to 3.04 (2H, m), 3.15 to 3.29 (2H, m), 3.40 (2H, t, J=6 Hz), 4.00 to 4.19 (2H, m), 4.45 (2H, s), 4.48 to 4.60 (1H, m), 6.21 (1H, br), 6.94 to 7.52 (15H, m), 9.96 (1H, br s), 10.71 (1H, br s)

(2) Boc-Gln-Trp-AzPhe(4-F)-NH(CH$_2$)$_2$OCH$_2$Ph

In the same manner as in Example 2 (2), the title compound was obtained from 250 mg of Boc-Trp-AzPhe(4-F)-NH(CH$_2$)$_2$OCH$_2$Ph, 1.00 ml of 4N HCl-AcOEt, 0.06 ml of Et$_3$N, 0.05 ml of NMM and 152 mg of Boc-Gln-ONp.

Yield: 230 mg; Rf$_1$: 0.45, Rf$_2$: 0.15; [α]$_D$: -14.00 (C=0.58, DMF) NMR (δ, DMSO-d$_6$, 55° C.): 1.34 (9H, s), 1.13 to 1.89 (2H, m), 2.07 to 2.14 (2H, m), 2.96 to 3.14 (4H, m), 3.39 (2H, t, J=6 Hz), 3.90 to 4.06 (2H, m), 4.33 to 4.39 (1H, m), 4.45 (2H, s), 4.50 (1H, d, J=15 Hz), 6.11 (1H, br), 6.63 (2H, br), 6.94 to 7.53 (15H, m), 8.10 (1H, br), 9.93 (1H, br), 10.75 (1H, br)

Example 31
t-Bu-NHCO-Gln-Trp-AzPhe(4-F)-NH(CH$_2$)$_2$OCH$_2$Ph
(t-Bu: t-butyl)

In the same manner as in Example 2 (2), the title compound was obtained from 140 mg of Boc-Gln-Trp-AzPhe(4-F)-NH(CH$_2$)$_2$OCH$_2$Ph of Example 30, 0.50 ml of 4N HCl-AcOEt, 0.03 ml of Et$_3$N and 0.03 ml of t-butyl isocyanate.

Yield: 74 mg; Rf$_1$: 0.40, Rf$_2$: 0.09; [α]$_D$: −14.27 (C=0.92, DMF) NMR (δ, DMSO-d$_6$, 55° C.): 1.18 (9H, s), 1.62 to 1.82 (2H, m), 2.07 (2H, t, J=8 Hz), 2.96 to 3.15 (4H, m), 3.39 (2H, t, J=6 Hz), 4.02 to 4.09 (2H, m), 4.30 to 4.37 (1H, m), 4.46 (2H, s), 4.52 (1H, d, J=15 Hz), 5.83 (2H, br s), 6.12 (1H, br), 6.58 (1H, br), 6.96 to 7.53 (15H, m), 8.19 (1H, br), 9.93 (1H, br s), 10.74 (1H, br s)

Example 32
Boc-Gln-Trp-AzTyr(CH$_2$Ph)-NHDmob (1) Boc-Trp-AzTyr(CH$_2$Ph)-NHDmob In the same manner as in Example 1 (1), the title compound was obtained from 2.90 g of Boc-AzTyr(CH$_2$Ph)-NHDmob, 1.05 g of 4-toluenesulfonic acid monohydrate and Boc-Trp-OH mixed acid anhydride (obtained by dissolving 1.70 g of Boc-Trp-OH in 20 ml of THF, adding 0.61 ml of NMM and 0.44 ml of isobutyl chloroformate to the solution under ice cooling and stirring the mixture for 1 hour).

Yield: 1.63 g; Rf$_3$: 0.22, Rf$_4$: 0.22; [α]$_D$: +4.32 (C=1.11, DMF) NMR (δ, CDCl$_3$, 55° C.): 1.34 (9H, s), 3.14 (2H, d, J=7 Hz), 3.75 (3H, s), 3.78 (3H, s), 4.21 to 4.31 (3H, m), 4.42 (1H, d, J=13 Hz), 4.62 (1H, d, J=13 Hz), 4.92 (1H, d, J=7 Hz), 5.00 (2H, s), 6.43 to 7.59 (19H, m), 7.75 (1H, br)

(2) Boc-Gln-Trp-AzTyr(CH2Ph)-NHDmob

In the same manner as in Example 2 (2), the title compound was obtained from 1.50 g of Boc-Trp-AzTyr(CH$_2$Ph)-NHDmob, 6.00 ml of 4N HCl-AcOEt, 0.30 ml of Et$_3$N, 0.23 ml of NMM and 780 mg of Boc-Gln-ONp.

Yield: 557 mg; Rf$_1$: 0.45, Rf$_2$: 0.15; [α]$_D$: −6.30 (C=1.30, DMF) NMR (δ, CDCl$_3$, 55° C.): 1.34 (9H, s), 1.86 to 1.92 (2H, m), 2.14 to 2.20 (2H, m), 3.18 (1H, dd, J=14 Hz, 7 Hz), 3.35 (1H, dd, J=14 Hz, 8 Hz), 3.75 (3H, s), 3.82 (3H, s), 3.89 to 4.05 (4H, m), 4.37 to 4.45 (1H, m), 4.67 (1H, d, J=15 Hz), 4.96 (2H, s), 5.65 (2H, br), 6.39 to 7.48 ($_2$OH, m), 7.93 (1H, br), 8.06 (1H, br)

Example 33
t-Bu-NHCO-Gln-Trp-AzPhe(2-Me)-NH(CH$_2$)$_2$OCH$_2$Ph
(t-Bu: t-butyl)

(1) Boc-Trp-AzPhe(2-Me)-NH(CH$_2$)$_2$OCH$_2$Ph

In the same manner as in Example 1 (1), the title compound was obtained from 4.50 g of Boc-AzPhe(2-Me)-NH(CH$_2$)$_2$OCH$_2$Ph, 2.07 g of 4-toluenesulfonic acid monohydrate and Boc-Trp-OH mixed acid anhydride (obtained by dissolving 3.30 g of Boc-Trp-OH in 30 ml of THF, adding 1.20 ml of NMM and 1.42 ml of isobutyl chloroformate to the solution under ice cooling and stirring the mixture for 1 hour).

Yield: 4.10 g; Rf$_3$: 0.21, Rf$_4$: 0.22; [α]$_D$: −16.88 (C=1.22, DMF) NMR (δ, DMSO-d$_6$, 55° C.): 1.31 (9H, s), 2.21 (3H, s), 2.86 to 2.91 (2H, m), 3.14 to 3.32 (2H, m), 3.41 (2H, t, J=6 Hz), 4.06 to 4.12 (1H, m), 4.30 to 4.38 (1H, m), 4.45 (2H, s), 4.65 (1H, d, J=16 Hz), 6.15 (1H, br), 6.80 to 7.51 (15H, m), 9.98 (1H, br s), 10.66 (1H, br s)

(2) Boc-Gln-Trp-Azphe(2-Me)-NH(CH$_2$)$_2$OCH$_2$Ph

In the same manner as in Example 2 (2), the title compound was obtained from 2.00 g of Boc-Trp-AzPhe(2-Me)-NH(CH$_2$)$_2$OCH$_2$Ph, 8.30 ml of 4N HCl-AcOEt, 0.47 ml of Et$_3$N and 1.22 g of Boc-Gln-ONp.

Yield: 1.56 g; Rf$_1$: 0.54, Rf$_2$: 0.30; [α]$_D$: −27.62 (C=1.24, DMF) NMR (δ, DMSO-d$_6$, 55° C.): 1.33 (9H, s), 1.63 to 1.88 (2H, m), 2.06 to 2.12 (2H, m), 2.19 (3H, s), 2.93 (1H, dd, J=15 Hz, 8 Hz), 3.02 (1H, dd, J=15 Hz, 6 Hz), 3.13 to 3.20 (2H, m), 3.39 (2H, t, J=6 Hz), 3.88 to 3.95 (1H, m), 4.30 to 4.42 (2H, m), 4.46 (2H, s), 4.60 (1H, d, J=15 Hz), 6.04 (1H, br), 6.62 (2H, br), 6.92 to 7.51 (15H, m), 8.01 (1H, br), 9.93 (1H, br s), 10.69 (1H, br s)

(3) t-Bu-NHCO-Gln-Trp-Azphe(2-Me)-NH(CH$_2$)$_2$OCH$_2$Ph

In the same manner as in Example 2 (2), the title compound was obtained from 500 mg of Boc-Gln-Trp-AzPhe(2-Me)-NH(CH$_2$)$_2$OCH$_2$Ph, 1.70 ml of 4N HCl-AcOEt, 0.10 ml of Et$_3$N and 68 mg of t-butyl isocyanate.

Yield: 456 mg; Rf$_1$: 0.53, Rf$_2$: 0.16; [α]$_D$: −27.65 (C=1.41, DMF) NMR (δ, DMSO-d$_6$, 55° C.): 1.18 (9H, s), 1.57 to 1.83 (2H, m), 2.06 (2H, t, J=8 Hz), 2.19 (3H, s), 2.95 (1H, dd, J=15 Hz, 8 Hz), 3.05 (1H, dd, J=15 Hz, 6 Hz), 3.14 to 3.21 (2H, m), 3.40 (2H, t, J=6 Hz), 4.00 to 4.07 (1H, m), 4.31 to 4.39 (2H, m), 4.46 (2H, s), 4.62 (1H, d, J=15 Hz), 5.81 to 5.86 (2H, m), 6.09 (1H, br), 6.56 (1H, br), 6.92 to 7.51 (15H, m), 8.12 (1H, br), 9.93 (1H, br s), 10.68 (1H, br s)

Example 34
t-Bu-NHCO-Gln-Trp-AzPhe(3-Me)-NH(CH$_2$)$_2$OCH$_2$Ph
(t-Bu: t-butyl)

(1) Boc-Trp-AzPhe(3-Me)-NH(CH$_2$)$_2$OCH$_2$Ph

In the same manner as in Example 1 (1), the title compound was obtained from 4.50 g of Boc-AzPhe(3-Me)-NH(CH$_2$)$_2$OCH$_2$Ph, 2.07 g of 4-toluenesulfonic acid monohydrate and Boc-Trp-OH mixed acid anhydride (obtained by dissolving 3.30 g of Boc-Trp-OH in 30 ml of THF, adding 1.20 ml of NMM and 1.42 ml of isobutyl chloroformate to the solution under ice cooling and stirring the mixture for 1 hour).

Yield: 4.75 g; Rf$_3$: 0.20, Rf$_4$: 0.20; [α]$_D$: −7.40 (C=1.21, DMF) NMR (δ, DMSO-d$_6$, 55° C.): 1.32 (9H, s), 2.24 (3H, s), 2.86 to 3.01 (2H, m), 3.15 to 3.31 (2H, m), 3.40 (2H, t, J=6 Hz), 4.02 to 4.14 (2H, m), 4.45 (2H, s), 4.59 (1H, d, J=15 Hz), 6.18 (1H, br), 6.85 to 7.53 (15H, m), 9.99 (1H, br s), 10.70 (1H, br s)

(2) Boc-Gln-Trp-AzPhe(3-Me)-NH(CH$_2$)$_2$OCH$_2$Ph

In the same manner as in Example 2 (2), the title compound was obtained from 2.00 g of Boc-Trp-AzPhe(3-Me)-NH(CH$_2$)$_2$OCH$_2$Ph, 8.30 ml of 4N HCl-AcOEt, 0.47 ml of Et$_3$N and 1.22 g of Boc-Gln-ONp.

Yield: 1.55 g; Rf$_1$: 0.54, Rf$_2$: 0.28; [α]$_D$: −20.49 (C=1.29, DMF) NMR (δ, DMSO-d$_6$, 55° C.): 1.34 (9H, s), 1.74 to 1.89 (2H, m), 2.07 to 2.13 (2H, m), 2.23 (3H, s), 2.98 (1H, dd, J=15 Hz, 8 Hz), 3.08 (1H, dd, J=15 Hz, 7 Hz), 3.11 to 3.20 (2H, m), 3.40 (2H, t, J=6 Hz), 3.90 to 3.97 (1H, m), 4.05 to 4.14 (1H, m), 4.34 to 4.42 (1H, m), 4.46 (2H, s), 4.55 (1H, d, J=15 Hz), 6.08 (1H, br), 6.61 (2H, br), 6.83 to 7.53 (15H, m), 8.04 (1H, br), 9.94 (1H, br s), 10.72 (1H, br s)

(3) t-Bu-NHCO-Gln-Trp-AzPhe(3-Me)-NH(CH$_2$)$_2$OCH$_2$Ph

In the same manner as in Example 2 (2), the title compound was obtained from 500 mg of Boc-Gln-Trp-AzPhe(3-Me)-NH(CH$_2$)$_2$OCH$_2$Ph, 1.70 ml of 4N HCl-AcOEt, 0.10 ml of Et$_3$N and 68 mg of t-butyl isocyanate.

Yield: 440 mg; Rf$_1$: 0.53, Rf$_2$: 0.16; [α]$_D$: −18.67 (C=1.24, DMF) NMR (δ, DMSO-d$_6$, 55° C.): 1.18 (9H, s), 1.58 to 1.82 (2H, m), 2.07 (2H, t, J=7 Hz), 2.23 (3H, s), 2.97 to 3.20 (4H, m), 3.40 (2H, t, J=6 Hz), 4.01 to 4.12 (2H, m), 4.31 to 4.37 (1H, m), 4.46 (2H, s), 4.56 (1H, d, J=15 Hz), 5.82 to 5.86 (2H, m), 6.12 (1H, br), 6.57 (1H, br), 6.84 to 7.52 (15H, m), 8.17 (1H, br), 9.94 (1H, br s), 10.71 (1H, br s)

Example 35
t-Bu-NHCO-Gln-Trp-AzPhe(4-Me)-NH(CH$_2$)$_2$OCH$_2$Ph
(t-Bu: t-butyl)

(1) Boc-Trp-AzPhe(4-Me)-NH(CH$_2$)$_2$OCH$_2$Ph

In the same manner as in Example 1 (1), the title compound was obtained from 4.50 g of Boc-AzPhe(4-Me)-NH(CH$_2$)$_2$OCH$_2$Ph, 2.07 g of 4-toluenesulfonic acid monohydrate and Boc-Trp-OH mixed acid anhydride (obtained by dissolving 3.30 g of Boc-Trp-OH in 30 ml of THF, adding 1.20 ml of NMM and 1.42 ml of isobutyl chloroformate to the solution under ice cooling and stirring the mixture for 1 hour).

Yield: 4.56 g; Rf$_3$: 0.18, Rf$_4$: 0.19; [α]$_D$: −5.82 (C=1.01, DMF) NMR (δ, DMSO-d$_6$, 55° C.): 1.32 (9H, s), 2.24 (3H, s), 2.90 (1H, dd, J=15 Hz, 8 Hz), 2.99 (1H, dd, J=15 Hz, 7 Hz), 3.19 to 3.31 (2H, m), 3.40 (2H, t, J=6 Hz), 4.04 to 4.17 (2H, m), 4.45 (2H, s), 4.58 (1H, d, J=15 Hz), 6.15 (1H, br), 6.89 to 7.52 (15H, m), 9.92 (1H, br s), 10.69 (1H, br s)

(2) Boc-Gln-Trp-AzPhe(4-Me)-NH(CH2)$_2$OCH$_2$Ph

In the same manner as in Example 2 (2), the title compound was obtained from 2.00 g of Boc-Trp-AzPhe(4-Me)-NH(CH$_2$)$_2$OCH$_2$Ph, 8.30 ml of 4N HCl-AcOEt, 0.47 ml of Et$_3$N and 1.22 g of Boc-Gln-ONp.

Yield: 1.72 g; Rf$_1$: 0.54, Rf$_2$: 0.26; [α]$_D$: −16.88 (C=1.26, DMF) NMR (δ, DMSO-d$_6$, 55° C.): 1.34 (9H, s), 1.65 to 1.90 (2H, m), 2.07 to 2.13 (2H, m), 2.24 (3H, s), 2.98 (1H, dd, J=15 Hz, 7 Hz), 3.08 (1H, dd, J=15 Hz, 7 Hz), 3.12 to 3.20 (2H, m), 3.39 (2H, t, J=7 Hz), 3.90 to 3.97 (1H, m), 4.05 to 4.14 (1H, m), 4.35 to 4.41 (1H, m), 4.46 (2H, s), 4.52 (1H, d, J=16 Hz), 6.06 (1H, br), 6.64 (2H, br), 6.90 to 7.53 (15H, m), 8.06 (1H, br), 9.90 (1H, br s), 10.73 (1H, br s)

(3) t-Bu-NHCO-Gln-Trp-AzPhe(4-Me)-NH(CH$_2$)$_2$OCH$_2$Ph

In the same manner as in Example 2 (2), the title compound was obtained from 500 mg of Boc-Gln-Trp-AzPhe(4-Me)-NH(CH$_2$)$_2$OCH$_2$Ph, 1.70 ml of 4N HCl-AcOEt, 0.10 ml of Et$_3$N and 68 mg of t-butyl isocyanate.

Yield: 472 mg; Rf$_1$: 0.53, Rf$_2$: 0.15; [α]$_D$: −15.34 (C=1.44, DMF) NMR (δ, DMSO-d$_6$, 55° C.): 1.19 (9H, s), 1.59 to 1.82 (2H, m), 2.07 (2H, t, J=8 Hz), 2.24 (3H, s), 2.96 to 3.19 (4H, m), 3.39 (2H, t, J=6 Hz), 4.02 to 4.12 (2H, m), 4.31 to 4.38 (1H, m), 4.46 (2H, s), 4.52 (1H, d, J=15 Hz), 5.82 to 5.86 (2H, m), 6.08 (1H, br), 6.58 (1H, br), 6.94 to 7.52 (1SH, m), 8.17 (1H, br), 9.90 (1H, br s), 10.72 (1H, br s)

Example 36
t-Bu-NHCO-Gln-Trp-AzPhe(4-iPr)-NH(CH$_2$)$_2$OCH$_2$Ph
(t-Bu: t-butyl)

(1) Boc-Trp-Azphe(4-iPr)-NH(CH$_2$)$_2$OCH$_2$Ph

In the same manner as in Example 1 (1), the title compound was obtained from 4.80 g of Boc-AzPhe(4-iPr)-NH(CH$_2$)$_2$OCH2Ph, 2.07 g of 4-toluenesulfonic acid monohydrate and Boc-Trp-OH mixed acid anhydride (obtained by dissolving 3.30 g of Boc-Trp-OH in 30 ml of THF, adding 1.20 ml of NMM and 1.42 ml of isobutyl chloroformate to the solution under ice cooling and stirring the mixture for 1 hour).

Yield: 4.11 g; Rf$_3$: 0.20, Rf$_4$: 0.20; [α]$_D$: −3.92 (C=1.07, DMF) NMR (δ, DMSO-d$_6$, 55° C.): 1.15 (3H, s), 1.17 (3H, s), 1.32 (9H, s), 2.78 to 3.03 (3H, m), 3.14 to 3.31 (2H, m), 3.40 (2H, t, J=6 Hz), 4.05 to 4.16 (2H, m), 4.45 (2H, s), 4.58 (1H, d, J=15 Hz), 6.14 (1H, br), 6.85 to 7.53 (15H, m), 9.95 (1H, br s), 10.70 (1H, br s)

(2) Boc-Gln-Trp-AzPhe(4-iPr)-NH(CH$_2$)$_2$OCH$_2$Ph

In the same manner as in Example 2 (2), the title compound was obtained from 2.00 g of Boc-Trp-AzPhe(4-iPr)-NH(CH2)$_2$OCH$_2$Ph, 8.00 ml of 4N HCl-AcOEt, 0.46 ml of Et$_3$N and 1.17 g of Boc-Gln-ONp.

Yield: 1.51 g; Rf$_1$: 0.54, Rf$_2$: 0.27; [α]$_D$: −15.38 (C=1.17, DMF) NMR (δ, DMSO-d$_6$, 55° C.): 1.15 (3H, s), 1.17 (3H, s), 1.34 (9H, s), 1.64 to 1.90 (2H, m), 2.07 to 2.14 (2H, m), 2.82 (1H, septet, J=7 Hz), 2.98 (1H, dd, J=15 Hz, 7 Hz), 3.08 (1H, dd, J=15 Hz, 7 Hz), 3.12 to 3.19 (2H, m), 3.39 (2H, t, J=6 Hz), 3.90 to 3.97 (1H, m), 4.06 to 4.15 (1H, m), 4.35 to 4.41 (1H, m), 4.46 (2H, s), 4.53 (1H, d, J=16 Hz), 6.04 (1H, br), 6.63 (2H, br), 6.94 to 7.53 (15H, m), 8.05 (1H, d, J=5 Hz), 9.94 (1H, br s), 10.73 (1H, br s)

(3) t-Bu-NHCO-Gln-Trp-AzPhe(4-iPr)-NH(CH$_2$)$_2$OCH$_2$Ph

In the same manner as in Example 2 (2), the title compound was obtained from 500 mg of Boc-Gln-Trp-AzPhe(4-iPr)-NH(CH$_2$)$_2$OCH$_2$Ph, 1.70 ml of 4N HCl-AcOEt, 0.10 ml of Et$_3$N and 66 mg of t-butyl isocyanate.

Yield: 449 mg; Rf$_1$: 0.53, Rf$_2$: 0.16; [α]$_D$: −14.14 (C=1.11, DMF) NMR (δ, DMSO-d$_6$, 55° C.): 1.15 (3H, s), 1.17 (3H, s), 1.18 (9H, s), 1.58 to 1.82 (2H, m), 2.07 (2H, t, J=8 Hz), 2.82 (1H, septet, J=7 Hz), 2.96 to 3.19 (4H, m), 3.39 (2H, t, J=6 Hz), 4.03 to 4.12 (2H, m), 4.32 to 4.38 (1H, m), 4.46 (2H, s), 4.53 (1H, d, J=16 Hz), 5.82 to 5.86 (2H, m), 6.08 (1H, br), 6.57 (1H, br), 6.93 to 7.53 (15H, m), 8.17 (1H, br), 9.94 (1H, br s), 10.73 (1H, br s)

Example 37
t-Bu-NHCO-Gln-Trp-AzPhe(2,4-diMe)-NH(CH$_2$)$_2$OCH$_2$Ph (t-Bu: t-butyl)

(1) Boc-Trp-Azphe(2,4-diMe)-NH(CH$_2$)$_2$OCH$_2$Ph

In the same manner as in Example 2 (1), the title compound was obtained from 700 mg of Boc-AzPhe(2,4-diMe)-NH(CH$_2$)$_2$OCH$_2$Ph, 4.10 ml of 4N HCl-AcOEt, 0.23 ml of Et$_3$N and Boc-Trp-OH mixed acid anhydride (obtained by dissolving 555 mg of Boc-Trp-OH in 5 ml of THF, adding 0.18 ml of NMM and 0.21 ml of isobutyl chloroformate to the solution under ice cooling and stirring the mixture for 1 hour).

Yield: 300 mg; Rf$_3$: 0.20, Rf$_4$: 0.23; [α]$_D$: −15.50 (C=1.10, DMF) NMR (δ, DMSO-d$_6$, 55° C.): 1.31 (9H, s), 2.18 (3H, s), 2.21 (3H, s), 2.84 to 2.92 (2H, m), 3.14 to 3.31 (2H, m), 3.40 (2H, t, J=6 Hz), 4.06 to 4.12 (1H, m), 4.30 (1H, d, J=15 Hz), 4.45 (2H, s), 4.62 (1H, d, J=15 Hz), 6.12 (1H, br), 6.82 to 7.50 (14H, m), 9.92 (1H, br s), 10.67 (1H, br s)

(2) Boc-Gln-Trp-AzPhe(2, 4-diMe)-NH(CH$_2$)$_2$OCH$_2$Ph

In the same manner as in Example 2 (2), the title compound was obtained from 250 mg of Boc-Trp-AzPhe(2,4-diMe)-NH(CH$_2$)$_2$OCH$_2$Ph, 1.03 ml of 4N HCl-AcOEt, 0.06 ml of Et3N, 0.05 ml of NMM and 151 mg of Boc-Gln-ONp.

Yield: 280 mg; Rf$_1$: 0.54, Rf$_2$: 0.30; [α]$_D$: −25.04 (C=1.19, DMF) NMR (δ, DMSO-d$_6$, 55° C.): 1.33 (9H, s), 1.62 to 1.88 (2H, m), 2.06 to 2.11 (2H, m), 2.15 (3H, s), 2.21 (3H, s), 2.92 (1H, dd, J=14 Hz, 8 Hz), 3.01 (1H, dd, J=14 Hz, 6 Hz), 3.13 to 3.19 (2H, m), 3.36 to 3.41 (2H, m), 3.89 to 3.95 (1H, m), 4.28 to 4.41 (2H, m), 4.45 (2H, s), 4.56 (1H, d, J=14 Hz), 6.01 (1H, br), 6.57 to 6.69 (2H, br), 6.80 to 7.50 (14H, m), 8.02 (1H, br s), 9.88 (1H, br s), 10.70 (1H, br s)

(3) t-Bu-NHCO-Gln-Trp-AzPhe(2, 4-diMe)-NH(CH$_2$)$_2$OCH$_2$Ph

In the same manner as in Example 2 (2), the title compound was obtained from 150 mg of Boc-Gln-Trp-AzPhe(2,4-diMe)-NH(CH$_2$)$_2$OCH$_2$Ph, 0.50 ml of 4N HCl-AcOEt, 0.03 ml of Et$_3$N and 0.03 ml of t-butyl isocyanate.

Yield: 120 mg; Rf$_1$: 0.53, Rf$_2$: 0.17; [α]$_D$: −25.71 (C=0.98, DMF) NMR (δ, DMSO-d$_6$, 55° C.): 1.18 (9H, s), 1.55 to 1.82 (2H, m), 2.06 (2H, t, J=8 Hz), 2.15 (3H, s), 2.20 (3H, s), 2.94 (1H, dd, J=15 Hz, 8 Hz), 3.04 (1H, dd, J=15 Hz, 6 Hz), 3.11 to 3.19 (2H, m), 3.39 (2H, t, J=6 Hz), 4.03 (1H, td, J=7 Hz, 7 Hz), 4.27 to 4.37 (2H, m), 4.46 (2H, s), 4.58 (1H, d, J=14 Hz), 5.81 to 5.85 (2H, m), 6.06 (1H, br), 6.56

(1H, br), 6.80 to 7.50 (14H, m), 8.13 (1H, br s), 9.88 (1H, br s), 10.70 (1H, br s)

Example 38
t-Bu-NHCO-Gln-Trp-AzPhe(2,5-diMe)-NH(CH$_2$)$_2$OCH$_2$Ph
(t-Bu: t-butyl)

(1) Boc-Trp-Azphe(2,5-diMe)-NH(CH$_2$)$_2$OCH$_2$Ph

In the same manner as in Example 2 (1), the title compound was obtained from 1.30 g of Boc-AzPhe(2,5-diMe)-NH(CH$_2$)$_2$OCH$_2$Ph, 7.60 ml of 4N HCl-AcOEt, 0.42 ml of Et$_3$N and Boc-Trp-OH mixed acid anhydride (obtained by dissolving 1.03 g of Boc-Trp-OH in 10 ml of THF, adding 0.33 ml of NMM and 0.40 ml of isobutyl chloroformate to the solution under ice cooling and stirring the mixture for 1 hour).

Yield: 500 mg; Rf$_3$: 0.22, Rf$_4$: 0.23; [α]$_D$: −16.27 (C=1.01, DMF) NMR (δ, DMSO-d$_6$, 55° C.): 1.31 (9H, s), 2.17 (6H, s), 2.84 to 2.87 (2H, m), 3.16 to 3.31 (2H, m), 3.41 (2H, t, J=6 Hz), 4.05 to 4.12 (1H, m), 4.35 (1H, br), 4.45 (2H, s), 4.62 (1H, d, J=15 Hz), 6.15 (1H, br), 6.85 to 7.51 (14H, m), 9.99 (1H, br s), 10.67 (1H, br s)

(2) Boc-Gln-Trp-AzPhe(2.5-diMe)-NH(CH$_2$)$_2$OCH$_2$Ph

In the same manner as in Example 2 (2), the title compound was obtained from 400 mg of Boc-Trp-AzPhe(2,5-diMe)-NH(CH$_2$)$_2$OCH$_2$Ph, 1.63 ml of 4N HCl-AcOEt, 0.09 ml of Et$_3$N, 0.07 ml of NMM and 240 mg of Boc-Gln-ONp.

Yield: 460 mg; Rf$_1$: 0.54, Rf$_2$: 0.30; [α]$_D$: −27.24 (C=1.27, DMF) NMR (δ, DMSO-d$_6$, 55° C.): 1.33 (9H, s), 1.62 to 1.87 (2H, m), 2.05 to 2.12 (2H, m), 2.14 (3H, s), 2.18 (3H, s), 2.89 to 3.02 (2H, m), 3.15 to 3.20 (2H, m), 3.37 to 3.41 (2H, m), 3.86 to 3.94 (1H, m), 4.30 to 4.42 (2H, m), 4.46 (2H, s), 4.59 (1H, d, J=14 Hz), 6.05 (1H, br), 6.56 to 6.70 (2H, br), 6.90 to 7.51 (14H, m), 8.00 (1H, br s), 9.95 (1H, br s), 10.69 (1H, br s)

(3) t-Bu-NHCO-Gln-Trp-AzPhe(2,5-diMe)-NH(CH$_2$)$_2$OCH$_2$Ph

In the same manner as in Example 2 (2), the title compound was obtained from 300 mg of Boc-Gln-Trp-AzPhe (2,5-diMe)-NH(CH$_2$)$_2$OCH$_2$Ph, 1.00 ml of 4N HCl-AcOEt, 0.06 ml of Et3N and 0.05 ml of t-butyl isocyanate.

Yield: 220 mg; Rf$_1$: 0.53, Rf$_2$: 0.18; [α]$_D$: −29.72 (C=1.11, DMF) NMR (δ, DMSO-d$_6$, 55° C.): 1.18 (9H, s), 1.55 to 1.81 (2H, m), 2.06 (2H, t, J=8 Hz), 2.15 (3H, s), 2.18 (3H, s), 2.89 to 3.05 (2H, m), 3.15 to 3.21 (2H, m), 3.41 (2H, t, J=6 Hz), 4.03 (1H, td, J=7 Hz, 7 Hz), 4.31 to 4.38 (2H, m), 4.47 (2H, s), 4.60 (1H, d, J=14 Hz), 5.81 to 5.84 (2H, m), 6.09 (1H, br), 6.57 (1H, br), 6.90 to 7.50 (14H, m), 8.12 (1H, br s), 9.95 (1H, br s), 10.68 (1H, br s)

Example 39
t-Bu-NHCO-Gln-Trp-Azphe(2-F)-NH(CH$_2$)$_2$OCH$_2$Ph
(t-Bu: t-butyl)

(1) Boc-Trp-Azphe(2-F)-NH(CH$_2$)$_2$OCH$_2$Ph

In 7 ml of THF was dissolved 550 mg of Boc-Trp-NHNHCH$_2$Ph(2-F), and 229 mg of PhCH$_2$O(CH$_2$)$_2$NCO was added to the solution under ice cooling. The mixture was stirred at room temperature for 18 hours and the solvent was removed. The residue was dissolved in AcOEt, washed successively with diluted hydrochloric acid, a saturated sodium hydrogen carbonate aqueous solution and a saturated saline solution, and then dried over anhydrous sodium sulfate. After the solvent was removed, the crude product obtained was recrystallized from AcOEt-hexane to obtain the title compound.

Yield: 710 mg; Rf$_3$: 0.20, Rf$_4$: 0.23; [α]$_D$: −14.24 (C=1.00, DMF) NMR (δ, DMSO-d$_6$, 55° C.): 1.31 (9H, s), 2.86 to 3.02 (2H, m), 3.15 to 3.32 (2H, m), 3.41 (2H, t, J=6 Hz), 4.09 to 4.16 (1H, m), 4.33 to 4.42 (1H, m), 4.45 (2H, s), 4.68 (1H, d, J=15 Hz), 6.22 (1H, br), 6.92 to 7.53 (15H, m), 10.10 (1H, br s), 10.68 (1H, br s)

(2) Boc-Gln-Trp-AzPhe(2-F)-NH(CH$_2$)$_2$OCH$_2$Ph

In the same manner as in Example 2 (2), the title compound was obtained from 500 mg of Boc-Trp-AzPhe(2-F)-NH(CH$_2$)$_2$-OCH$_2$Ph, 2.10 ml of 4N HCl-AcOEt, 0.12 ml of Et$_3$N, 0.09 ml of NMM and 305 mg of Boc-Gln-ONp.

Yield: 550 mg; Rf$_1$: 0.53, Rf$_2$: 0.27; [α]$_D$: −22.40 (C=1.02, DMF) NMR (δ, DMSO-d$_6$, 55° C.): 1.33 (9H, s), 1.63 to 1.89 (2H, m), 2.06 to 2.12 (2H, m), 2.97 (1H, dd, J=15 Hz, 8 Hz), 3.07 (1H, dd, J=15 Hz, 6 Hz), 3.14 to 3.20 (2H, m), 3.40 (2H, t, J=6 Hz), 3.88 to 3.96 (1H, m), 4.33 to 4.42 (2H, m), 4.46 (2H, s), 4.65 (1H, d, J=15 Hz), 6.11 (1H, br), 6.61 (1H, br), 6.68 (1H, br), 6.92 to 7.53 (15H, m), 8.05 (1H, br), 10.04 (1H, br s), 10.70 (1H, br s)

(3) t-Bu-NHCO-Gln-Trp-AzPhe(2-F)-NH(CH$_2$)$_2$OCH$_2$Ph

In the same manner as in Example 2 (2), the title compound was obtained from 300 mg of Boc-Gln-Trp-AzPhe (2-F)-NH(CH$_2$)$_2$OCH$_2$Ph, 1.03 ml of 4N HCl-AcOEt, 0.06 ml of Et$_3$N and 0.05 ml of t-butyl isocyanate.

Yield: 270 mg; Rf$_1$: 0.51, Rf$_2$: 0.16; [α]$_D$: −26.55 (C=1.49, DMF) NMR (δ, DMSO-d$_6$, 55° C.): 1.18 (9H, s), 1.58 to 1.82 (2H, m), 2.06 (2H, t, J=7 Hz), 3.00 (1H, dd, J=15 Hz, 8 Hz), 3.10 (1H, dd, J=15 Hz, 6 Hz), 3.15 to 3.21 (2H, m), 3.40 (2H, t, J=6 Hz), 4.02 (1H, td, J=7 Hz, 7 Hz), 4.32 to 4.39 (2H, m), 4.47 (2H, s), 4.67 (1H, d, J=16 Hz), 5.82 to 5.87 (2H, m), 6.15 (1H, br), 6.57 (1H, br), 6.92 to 7.52 (15H, m), 8.16 (1H, br), 10.04 (1H, br s), 10.70 (1H, br s)

Example 40
t-Bu-NHCO-Gln-Trp-AzPhe(2-CF$_3$)-NH(CH$_2$)$_2$OCH$_2$Ph
(t-Bu: t-butyl)

(1) Boc-Trp-AzPhe(2-CF$_3$)-NH(CH$_2$)$_2$OCH$_2$Ph

In the same manner as in Example 39 (1), the title compound was obtained from 1.03 g of Boc-Trp-NHNHCH$_2$Ph(2-CF$_3$) and 385 mg of PhCH$_2$O(CH$_2$)$_2$NCO.

Yield: 1.24 g; Rf$_3$: 0.24, Rf$_4$: 0.30; [α]$_D$: −10.67 (C=1.03, DMF) NMR (δ, DMSO-d$_6$, 55° C.): 1.30 (9H, s), 2.87 to 3.02 (2H, m), 3.16 to 3.31 (2H, m), 3.42 (2H, t, J=6 Hz), 4.10 to 4.17 (1H, m), 4.46 (2H, s), 4.53 to 4.62 (1H, m), 4.80 (1H, d, J=16 Hz), 6.30 (1H, br), 6.88 to 7.66 (15H, m), 10.21 (1H, br s), 10.65 (1H, br s)

(2) Boc-Gln-Trp-AzPhe(2-CF$_3$)-NH(CH$_2$)$_2$OCH$_2$Ph

In the same manner as in Example 2 (2), the title compound was obtained from 800 mg of Boc-Trp-AzPhe(2-CF$_3$)-NH(CH$_2$)$_2$OCH$_2$Ph, 3.10 ml of 4N HCl-AcOEt, 0.17 ml of Et$_3$N, 0.13 ml of NMM and 450 mg of Boc-Gln-ONp.

Yield: 800 mg; Rf$_1$: 0.54, Rf$_2$: 0.32; [α]$_D$: −19.33 (C=1.20, DMF) NMR (δ, DMSO-d$_6$, 55° C.): 1.33 (9H, s), 1.62 to 1.88 (2H, m), 2.06 to 2.12 (2H, m), 2.98 (1H, dd, J=15 Hz, 8 Hz), 3.07 (1H, dd, J=15 Hz, 7 Hz), 3.15 to 3.22 (2H, m), 3.42 (2H, t, J=6 Hz), 3.87 to 3.95 (1H, m), 4.36 to 4.43 (1H, m), 4.47 (2H, s), 4.47 to 4.56 (1H, m), 4.80 (1H, d, J=15 Hz), 6.24 (1H, br), 6.61 (1H, br), 6.76 (1H, br), 6.88 to 7.66 (15H, m), 8.09 (1H, br), 10.13 (1H, br s), 10.66 (1H, br s)

(3) t-Bu-NHCO-Gln-Trp-Azphe(2-CF$_3$)-NH(CH$_2$)$_2$OCH$_2$Ph

In the same manner as in Example 2 (2), the title compound was obtained from 400 mg of Boc-Gln-Trp-AzPhe (2-CF$_3$)-NH(CH$_2$)$_2$OCH$_2$Ph, 1.28 ml of 4N HCl-AcOEt, 0.07 ml of Et$_3$N and 0.06 ml of t-butyl isocyanate.

Yield: 360 mg; Rf$_1$: 0.52, Rf$_2$: 0.19; [α]$_D$: −27.13 (C=1.16, DMF) NMR (δ, DMSO-d$_6$, 55° C.): 1.18 (9H, s), 1.56 to 1.81 (2H, m), 2.06 (2H, t, J=8 Hz), 3.03 (1H, dd, J=15 Hz, 8 Hz), 3.12 (1H, dd, J=15 Hz, 6 Hz), 3.15 to 3.24 (2H, m), 3.43 (2H, t, J=6 Hz), 3.98 (1H, td, J=7 Hz, 7 Hz), 4.32 to 4.39 (1H, m), 4.48 (2H, s), 4.54 (1H, d, J=17 Hz), 4.83 (1H, d, J=17 Hz), 5.84 to 5.90 (2H, m), 6.31 (1H, br), 6.57 (1H, br), 6.88 to 7.66 (15H, m), 8.17 (1H, br), 10.13 (1H, br s), 10.66 (1H, br s)

Example 41 t-Bu-NHCO-Gln-Trp-AzPhe-NH($CH_2$)$_2$O-(2-naphthylmethyl) (t-Bu:t-butyl)

(1) Boc-Trp-AzPhe-NH($CH_2$)$_2$O-(2-naphthylmethyl)

In the same manner as in Example 2 (1), the title compound was obtained from 3.98 g of Boc-AzPhe-NH($CH_2$)$_2$O-(2-naphthylmethyl), 22.90 ml of 4N HCl-AcOEt, 1.28 ml of $Et_3N$ and Boc-Trp-OH mixed acid anhydride (obtained by dissolving 3.11 g of Boc-Trp-OH in 30 ml of THF, adding 1.01 ml of NMM and 1.19 ml of isobutyl chloroformate to the solution under ice cooling and stirring the mixture for 1 hour).

Yield: 2.44 g; $Rf_3$: 0.17, $Rf_4$: 0.19; $[\alpha]_D$: −8.03 (C=1.17, DMF) NMR (δ, DMSO-$d_6$, 55° C.): 1.29 (9H, s), 2.91 (1H, dd, J=15 Hz, 8 Hz), 2.99 (1H, dd, J=15 Hz, 7 Hz), 3.16 to 3.35 (2H, m), 3.46 (2H, t, J=6 Hz), 4.09 to 4.15 (2H, m), 4.60 to 4.65 (1H, m), 4.63 (2H, s), 6.22 (1H, br), 6.92 to 7.88 (18H, m), 10.00 (1H, br s), 10.70 (1H, br s)

(2) Boc-Gln-Trp-AzPhe-NH($CH_2$)$_2$O-(2-naphthylmethyl)

In the same manner as in Example 2 (2), the title compound was obtained from 1.08 g of Boc-Trp-AzPhe-NH($CH_2$)$_2$O-(2-naphthylmethyl), 4.35 ml of 4N HCl-AcOEt, 0.25 ml of $Et_3N$, 0.19 ml of NMM and 671 mg of Boc-Gln-ONp.

Yield: 1.09 g; $Rf_1$: 0.54, $Rf_2$: 0.29; $[\alpha]_D$: −15.10 (C=1.16, DMF) NMR (δ, DMSO-$d_6$, 55° C.): 1.33 (9H, s), 1.65 to 1.90 (2H, m), 2.08 to 2.14 (2H, m), 2.99 (1H, dd, J=14 Hz, 7 Hz), 3.09 (1H, dd, J=14 Hz, 7 Hz), 3.14 to 3.23 (2H, m), 3.46 (2H, t, J=6 Hz), 3.91 to 3.99 (1H, m), 4.11 to 4.18 (1H, m), 4.36 to 4.42 (1H, m), 4.58 (1H, d, J=14 Hz), 4.63 (2H, s), 6.12 (1H, br), 6.56 to 6.72 (2H, br), 6.93 to 7.88 (18H, m), 8.07 (1H, br), 9.96 (1H, br s), 10.73 (1H, br s)

(3) t-Bu-NHCO-Gln-Trp-AzPhe-NH($CH_2$)$_2$O-(2-naphthylmethyl)

In the same manner as in Example 2 (2), the title compound was obtained from 500 mg of Boc-Gln-Trp-AzPhe-NH($CH_2$)$_2$O-(2-naphthylmethyl), 1.68 ml of 4N HCl-AcOEt, 0.09 ml of $Et_3N$ and 0.08 ml of t-butyl isocyanate.

Yield: 350 mg; $Rf_1$: 0.53, $Rf_2$: 0.18; $[\alpha]_D$: −14.11 (C=1.19, DMF) NMR (δ, DMSO-$d_6$, 55° C.): 1.18 (9H, s), 1.61 to 1.82 (2H, m), 2.08 (2H, t, J=8 Hz), 2.98 to 3.25 (4H, m), 3.47 (2H, t, J=6 Hz), 4.02 to 4.09 (1H, m), 4.16 (1H, d, J=15 Hz), 4.32 to 4.39 (1H, m), 4.57 (1H, d, J=15 Hz), 4.64 (2H, s), 5.82 to 5.87 (2H, m), 6.15 (1H, br), 6.56 (1H, br), 6.93 to 7.87 (18H, m), 8.17 (1H, d, J=5 Hz), 9.96 (1H, br s), 10.71 (1H, br s)

Example 42 t-Bu-NHCO-Gln-Trp-AzPhe-NH($CH_2$)$_2$O-(3-pyridylmethyl) (t-Bu:t-butyl)

(1) Boc-Trp-AzPhe-NH($CH_2$)$_2$O-(3-pyridylmethyl)

In 10 ml of anhydrous DMF was dissolved 1.50 g of Boc-Trp-NHNH$CH_2$Ph. Under ice cooling, to the solution was added a 2-(3-pyridylmethoxy)ethyl isocyanate solution prepared separately (obtained by dissolving 800 mg of 3-(3-pyridylmethoxy)propionic acid in 10 ml of anhydrous DMF, adding 0.80 ml of diphenylphosphorylazide and 1.04 ml of $Et_3N$ to the solution and stirring the mixture at 80° C. for 2 hours), and the mixture was stirred at room temperature for 18 hours. Subsequent procedures were carried out in the same manner as in Example 2 (2) to obtain the title compound.

Yield: 1.73 g; $Rf_1$: 0.61, $Rf_2$: 0.42; $[\alpha]_D$: −9.92 (C=1.31, DMF) NMR (δ, DMSO-$d_6$, 55° C.): 1.32 (9H, s), 2.90 (1H, dd, J=15 Hz, 8 Hz), 2.99 (1H, dd, J=15 Hz, 7 Hz), 3.07 to 3.32 (2H, m), 3.43 (2H, t, J=6 Hz), 4.07 to 4.15 (2H, m), 4.49 (2H, s), 4.62 (1H, d, J=15 Hz), 6.20 (1H, br), 6.93 to 7.34 (11H, m), 7.51 (1H, d, J=8 Hz), 7.70 (1H, d, J=8 Hz), 8.46 (1H, d, J=5 Hz), 8.51 (1H, s), 9.99 (1H, br s), 10.70 (1H, br s)

(2) Boc-Gln-Trp-AzPhe-NH($CH_2$)$_2$O-(3-pyridylmethyl)

In the same manner as in Example 2 (2), the title compound was obtained from 1.00 g of Boc-Trp-AzPhe-NH($CH_2$)$_2$O-(3-pyridylmethyl), 4.25 ml of 4N HCl-AcOEt, 0.48 ml of $Et_3N$, 0.19 ml of NMM and 656 mg of Boc-Gln-ONp.

Yield: 1.16 g; $Rf_1$: 0.44, $Rf_2$: 0.14; $[\alpha]_D$: −22.53 (C=1.04, DMF) NMR (δ, DMSO-$d_6$, 55° C.): 1.34 (9H, s), 1.63 to 1.89 (2H, m), 2.06 to 2.16 (2H, m), 2.98 (1H, dd, J=15 Hz, 7 Hz), 3.08 (1H, dd, J=15 Hz, 7 Hz), 3.12 to 3.21 (2H, m), 3.42 (2H, t, J=6 Hz), 3.90 to 3.97 (1H, m), 4.12 (1H, d, J=15 Hz), 4.34 to 4.40 (1H, m), 4.50 (2H, s), 4.57 (1H, d, J=15 Hz), 6.11 (1H, br), 6.59 (1H, br), 6.70 (1H, br), 6.94 to 7.34 (11H, m), 7.51 (1H, d, J=8 Hz), 7.71 (1H, d, J=8 Hz), 8.08 (1H, d, J=5 Hz), 8.46 to 8.53 (1H, m), 8.53 (1H, s), 9.96 (1H, br s), 10.73 (1H, br s)

(3) t-Bu-NHCO-Gln-Trp-AzPhe-NH($CH_2$)$_2$O-(3-pyridylmethyl)

In the same manner as in Example 2 (2), the title compound was obtained from 500 mg of Boc-Gln-Trp-AzPhe-NH($CH_2$)$_2$O-(3-pyridylmethyl), 1.75 ml of 4N HCl-AcOEt, 0.20 ml of $Et_3N$ and 0.08 ml of t-butyl isocyanate.

Yield: 440 mg; $Rf_1$: 0.36, $Rf_2$: 0.07; $[\alpha]_D$: −20.37 (C=1.08, DMF) NMR (δ, DMSO-$d_6$, 55° C.): 1.18 (9H, s), 1.59 to 1.82 (2H, m), 2.07 (2H, t, J=8 Hz), 2.97 to 3.22 (4H, m), 3.43 (2H, t, J=6 Hz), 4.02 to 4.15 (2H, m), 4.30 to 4.38 (1H, m), 4.50 (2H, s), 4.57 (1H, d, J=16 Hz), 5.82 to 5.86 (2H, m), 6.14 (1H, br), 6.57 (1H, br), 6.94 to 7.34 (l1H, m), 7.51 (1H, d, J=8 Hz), 7.72 (1H, d, J=8 Hz), 8.17 (1H, br), 8.47 (1H, d, J=4 Hz), 8.53 (1H, s), 9.95 (1H, br s), 10.72 (1H, br s)

Example 43

Boc-Gln-Trp-AzPhe-NH($CH_2$)$_2$O-benzhydryl

In 3 ml of MeOH, 130 mg of Boc-Gln-Trp-AzPhe-OBzl was stirred in the presence of 13 mg of 10% palladium carbon for 18 hours in a hydrogen stream. After palladium carbon was separated by filtration, the solvent was removed. The residue was dried under reduced pressure and then dissolved in 3 ml of anhydrous DMF. Under ice cooling, to the solution was added a 2-benzhydryloxyethyl isocyanate solution prepared separately (obtained by dissolving 64 mg of 3-benzhydryloxypropionic acid in 3 ml of anhydrous DMF, adding 68 mg of diphenylphosphorylazide and 0.03 ml of $Et_3N$ to the solution and stirring the mixture at 80° C. for 2 hours), and the mixture was stirred at room temperature for 18 hours. Subsequent procedures were carried out in the same manner as in Example 2 (2) to obtain the title compound.

Yield: 55 mg; $Rf_1$: 0.54, $Rf_2$: 0.32; $[\alpha]_D$: −15.52 (C=0.57, DMF) NMR (δ, DMSO-$d_6$, 55° C.): 1 .34 (9H, s), 1. 62 to 1 .83 (2H, m), 2.05 to 2.11 (2H, m), 2.94 to 3.15 (4H, m), 3.33 (2H, t, J=6 Hz), 3.87 to 3.95 (1H, m), 4.09 to 4.17 (1H, m), 4.33 to 4.40 (1H, m), 4.50 to 4.57 (1H, m), 5.43 (1H, s), 6.09 (1H, br), 6.62 (2H, br), 6.93 to 7.52 (21H, m), 8.06 (1H, br), 9.92 (1H, br), 10.72 (1H, br)

Example 44 t-Bu-NHCO-Gln-Trp-AzPhe-NH($CH_2$)$_2$O-benzhydryl (t-Bu: t-butyl)

(1) t-Bu-NHC O-Gln-Trp-AzPhe-OBzl

In the same manner as in Example 2 (2)1, the title compound was obtained from 12.00 g of Boc-Gln-Trp- AzPhe-OBzl, 7.45 ml of 4N HCl-AcOEt, 0.42 ml of Et$_3$N and 0.34 ml of t-butyl isocyanate.

Yield: 1.88 g; Rf$_1$: 0.52, Rf$_2$: 0.16; [α]$_D$: −5.36 (C=1.23, DMF) NMR (δ, DMSO-d$_6$, 55° C.): 1.19 (9H, s), 1.58 to 1.85 (2H, m), 2.05 (2H, t, J=8 Hz), 2.85 to 3.08 (2H, m), 4.04 to 4.11 (1H, m), 4.43 to 4.60 (3H, m), 5.09 (2H, s), 5.80 to 5.82 (2H, m), 6.55 (1H, br), 6.92 to 7.31 (15H, m), 7.51 (1H, d, J=8 Hz), 7.88 (1H, d, J=8 Hz), 10.30 (1H, br s), 10.62 (lH, br s)

(2) t-Bu-NHCO-Gln-Trp-AzPhe-NH(CH$_2$)$_2$O-benzhydryl

In 3 ml of MeOH, 130 mg of t-Bu-NHCO-Gln-Trp-AzPhe-OBzl was stirred in the presence of 13 mg of 10% palladium carbon for 18 hours in a hydrogen stream. After palladium carbon was separated by filtration, the solvent was removed. The residue was dried under reduced pressure and then dissolved in 3 ml of anhydrous DMF. Under ice cooling, to the solution was added a 2-benzhydryloxyethyl isocyanate solution prepared separately (obtained by dissolving 55 mg of 3-benzhydryloxypropionic acid in 3 ml of anhydrous DMF, adding 58 mg of diphenylphosphorylazide and 0.03 ml of Et$_3$N to the solution and stirring the mixture at 80° C. for 2 hours), and the mixture was stirred at room temperature for 18 hours. Subsequent procedures were carried out in the same manner as in Example 2 (2) to obtain the title compound.

Yield: 75 mg; Rf$_1$: 0.53, Rf$_2$: 0.20; [α]$_D$: −19.14 (C=0.47, DMF) NMR (δ, DMSO-d$_6$, 55° C.): 1.18 (9H, s), 1.55 to 1.80 (2H, m), 2.05 (2H, t, J=7 Hz), 2.97 to 3.19 (4H, m), 3.35 (2H, t, J=6 Hz), 3.87 to 3.92 (1H, m), 4.18 (1H, d, J=14 Hz), 4.31 to 4.38 (1H, m), 4.55 (1H, d, J=14 Hz), 5.44 (1H, s), 5.82 to 5.86 (2H, m), 6.12 (1H, br), 6.57 (1H, br), 6.93 to 7.52 (21H, m), 8.13 (1H, br), 9.91 (1H, br s), 10.71 (1H, br s)

Test example 1

The activity of the azapeptide derivative of the present invention to a NKA receptor was evaluated by the following method.

(1) Activity to constriction of hamster respiratory tracts caused by NKA

Respiratory tracts were taken out from male Syrian strain Golden hamsters having a body weight of 100 to 180 g, and cyclic specimens having a width of 3 to 6 mm were prepared. The specimens were incubated at 37° C. and suspended by loading a static tension of 0.5 g, in a reaction tank charged with 15 ml of a Tyrode solution (137 mM of NaCl, 2.7 mM of KCl, 1.8 mM of CaCl$_2$, 1.02 mM of MgCl$_2$, 11.9 mM of NaHCO$_3$, 0.42 mM of NaH$_2$PO$_4$ and 5.5 mM of glucose) in which 95% O$_2$-5% CO$_2$ had been passed.

The compound to be tested was charged into the reaction tank and maintained for 5 minutes. 1×10$^{-7}$M of NKA was charged into the reaction tank, and tension caused thereby was recorded. The examined effect of the tested compound as an antagonist was shown by IC$_{50}$. This IC$_{50}$ is shown by a mole concentration of an antagonist exhibiting 50% of control to tension caused by adding 1×10$^{-7}$M of NKA when the antagonist was not added. The results obtained are shown in Table 1.

TABLE 1

| | IC$_{50}$ (M) | | IC$_{50}$ (M) |
|---|---|---|---|
| Example 1 (3) | 4.5 × 10$^{-8}$ | Example 21 | 1.7 × 10$^{-9}$ |
| Example 2 (1) | 3.1 × 10$^{-7}$ | Example 22 | 4.9 × 10$^{-6}$ |
| Example 2 (2) | 6.6 × 10$^{-10}$ | Example 23 (3) | 7.8 × 10$^{-8}$ |

TABLE 1-continued

| | IC$_{50}$ (M) | | IC$_{50}$ (M) |
|---|---|---|---|
| Example 2 (3) | 1.9 × 10$^{-9}$ | Example 24 (2) | 4.6 × 10$^{-8}$ |
| Example 3 | 6.0 × 10$^{-10}$ | Example 25 (3) | 3.4 × 10$^{-8}$ |
| Example 4 | 2.3 × 10$^{-9}$ | Example 26 (3) | 8.3 × 10$^{-7}$ |
| Example 5 | 2.2 × 10$^{-9}$ | Example 27 (3) | 9.9 × 10$^{-7}$ |
| Example 6 | 6.0 × 10$^{-10}$ | Example 28 (3) | 2.7 × 10$^{-8}$ |
| Example 7 | 5.0 × 10$^{-10}$ | Example 29 (3 | 1.9 × 10$^{-7}$ |
| Example 8 | 7.0 × 10$^{-10}$ | Example 30 (2) | 1.1 × 10$^{-9}$ |
| Example 9 | 1.4 × 10$^{-9}$ | Example 31 | 4.2 × 10$^{-10}$ |
| Example 10 | 6.8 × 10$^{-9}$ | Example 32 (2) | 7.7 × 10$^{-6}$ |
| Example 11 | 8.9 × 10$^{-9}$ | Example 33 (3) | 1.6 × 10$^{-10}$ |
| Example 12 | 4.5 × 10$^{-9}$ | Example 34 (3) | 3.9 × 10$^{-9}$ |
| Example 13 (1) | 8.0 × 10$^{-8}$ | Example 35 (3) | 8.2 × 10$^{-10}$ |
| Example 13 (2) | 7.8 × 10$^{-8}$ | Example 36 (3) | 6.9 × 10$^{-8}$ |
| Example 14 | 2.4 × 10$^{-8}$ | Example 37 (3) | 2.7 × 10$^{-10}$ |
| Example 15 | 3.5 × 10$^{-8}$ | Example 38 (3) | 6.8 × 10$^{-10}$ |
| Example 16 (1) | 1.3 × 10$^{-8}$ | Example 39 (3) | 6.1 × 10$^{-10}$ |
| Example 16 (2) | 1.3 × 10$^{-8}$ | Example 40 (3) | 3.1 × 10$^{-10}$ |
| Example 17 (2) | 2.9 × 10$^{-8}$ | Example 41 (3) | 2.0 × 10$^{-8}$ |
| Example 17 (3) | 4.2 × 10$^{-9}$ | Example 42 (3) | 1.6 × 10$^{-8}$ |
| Example 18 (2) | 5.6 × 10$^{-9}$ | Example 44 (2) | 2.3 × 10$^{-7}$ |
| Example 19 (3) | 5.3 × 10$^{-9}$ | Reference example 13 | 2.2 × 10$^{-8}$ |
| Example 20 (3) | 1.7 × 10$^{-9}$ | Reference example 14 | 3.3 × 10$^{-7}$ |

(2) Activity to constriction of guinea pig respiratory tracts caused by NKA

Male Hartley strain guinea pigs having a body weight of 350 to 500 g were anesthetized by administering 1.5 g/kg of urethane into abdominal cavities thereof. Cannulas made of polyethylene were inserted into cervical veins and respiratory tracts. From the cervical vein cannulas, 1 mg of gallamine was administered to stop respiration. The respiratory tract cannulas were connected to a respirator, and artificial respiration was carried out with an air-supplying amount at one time of 4 to 6 ml and an air-supplying frequency of 70 times/min. Side branches of the respiratory tract cannulas were introduced into a water tank, and a hydraulic pressure of 8 cm H$_2$O was loaded. Excess air amounts exceeding the above hydraulic pressure and discharged were measured. From the cervical vein cannulas, 2 nmol/kg of NKA was administered, each compound to be tested was administered after 15 minutes, and further 2 nmol/kg of NKA was administered after 1, 15, 30, 45 and 60 minutes, respectively. The increased amounts of excess air after the respective NKA administrations were measured, and percentages relative to the increased amounts of excess air when the respiratory tracts were completely closed were determined, which were defined as respiratory constriction rates. The decreased ratios of the respiratory constriction rates after administering the compounds to be tested to the respiratory constriction rates before administering the compounds to be tested were shown by percentages, which were defined as controlling rates. The controlling rates were regarded as an effect of the compound to be tested as an antagonist. The results obtained are shown in Table 2.

TABLE 2

| | Controlling rate (%) | | | | |
|---|---|---|---|---|---|
| | 1 min | 15 min | 30 min | 45 min | 60 min |
| Example 1 (3) | 22.3 | 16.5 | — | — | — |
| Example 2 (2) | 80.2 | 83.5 | 66.5 | 68.5 | 54.9 |
| Example 2 (3) | 27.4 | 66.0 | 59.5 | 48.9 | 53.7 |
| Example 3 | 100.0 | 96.6 | 87.2 | 79.6 | 65.0 |
| Example 4 | 92.4 | 91.9 | 91.2 | 91.2 | 91.2 |

TABLE 2-continued

| | Controlling rate (%) | | | | |
|---|---|---|---|---|---|
| | 1 min | 15 min | 30 min | 45 min | 60 min |
| Example 5 | 100.0 | 100.0 | 89.5 | 88.8 | 88.2 |
| Example 6 | 100.0 | 100.0 | 84.1 | 84.1 | 82.9 |
| Example 7 | 100.0 | 93.7 | 86.8 | 85.9 | 78.4 |
| Example 8 | 17.8 | 85.1 | 91.4 | 82.7 | 82.7 |
| Example 9 | 100.0 | 100.0 | 88.0 | 88.0 | 80.8 |
| Example 10 | 64.3 | 53.5 | 43.6 | 32.3 | 39.8 |
| Example 12 | 19.5 | 73.2 | 62.2 | 54.8 | 51.7 |
| Example 28 (3) | 54.1 | 30.0 | — | — | — |
| Example 30 (2) | 76.8 | 81.1 | 72.2 | 58.3 | 61.3 |
| Example 31 | 100.0 | 86.8 | 79.4 | 77.6 | 58.7 |
| Example 33 (3) | 79.8 | 86.5 | 92.9 | 85.8 | 70.1 |
| Example 34 (3) | 82.6 | 100.0 | 100.0 | 100.0 | 100.0 |
| Example 35 (3) | 100.0 | 86.2 | 92.6 | 68.0 | 65.4 |
| Example 37 (3) | 40.1 | 80.1 | 79.0 | 70.4 | 60.6 |
| Example 38 (3) | 63.9 | 92.3 | 95.9 | 86.6 | 72.0 |
| Example 39 (3) | 95.6 | 90.5 | 79.7 | 52.6 | 39.7 |
| Example 40 (3) | 100.0 | 100.0 | 100.0 | 91.7 | 91.7 |
| Reference example 13 peptide III | 11.9 | 3.9 | — | — | — |

We claim:

1. An azapeptide compound represented by the formula (I):

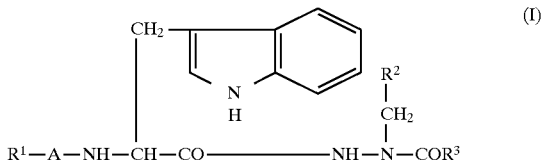

wherein A represents a direct bond, an α-amino acid or a residue of a dipeptide; $R^1$ represents a hydrogen atom or a protective group for a terminal amino group;

$R^2$ represents a phenyl group or a phenyl group substituted by one or two substituents selected from the group consisting of a lower alkyl group, halogen atom, hydroxyl group which may be protected, nitro group, amino group which may be protected and perhalo lower alkyl group; and $R^3$ represents a hydroxyl group or a protective group for a terminal carboxyl group, and a salt thereof.

2. The compound and a salt thereof according to claim 1, wherein the α-amino acid or a residue of the dipeptide of A is a natural α-amino acid or a residue of a dipeptide thereof.

3. The compound and a salt thereof according to claim 1, wherein A is a natural α-amino acid selected from the group consisting of glycine, alanine, valine, leucine, isoleucine, serine, methionine, threonine, phenylalanine, tyrosine, tryptophan, cysteine, cystine, proline, 4-hydroxyproline, histidine, aspartic acid, asparagine, glutamic acid, glutamine arginine, citrulline, ornithine and lysine, or a residue of a dipeptide thereof.

4. The compound and a salt thereof according to claim 3, wherein A is methionine, aspartic acid, asparagine, glutamic acid, glutamine, arginine, citrulline or ornithine, or a residue of a dipeptide thereof.

5. The compound and a salt thereof according to claim 4, wherein the dipeptide is aspartic acid-glutamine or asparagine-glutamine.

6. The compound and a salt thereof according to claim 1, wherein $R^2$ is a phenyl group, a substituted phenyl group substituted by one or two substituents selected from the group consisting of an alkyl group having 1 to 4 carbon atoms, halogen atom, hydroxyl group which may be protected, or perhalo alkyl group having 1 to 4 carbon atoms.

7. The compound and a salt thereof according to claim 1, wherein $R^3$ represents a formula of —$OR^4$ or a formula of —$N(R^5)(R^6)$ where $R^4$, $R^5$ and $R^6$ each represent a hydrogen atom, a substituted or unsubstituted alkyl group having 1 to 4 carbon atoms or an aralkyl group, or $R^5$ and $R^6$ may be bonded with a nitrogen atom to which they are bonded, to form a hetero saturated monocyclic ring.

8. The compound and a salt thereof according to claim 7, wherein $R^4$ is an aralkyl group; or $R^5$ is an alkyl group having 1 to 4 carbon atoms which may be substituted by a hydroxy or aralkyloxy group, or an aralkyl group which may be substituted by a halogen or an alkoxy group having 1 to 5 carbon atoms and $R^6$ is a hydrogen atom.

9. The compound and a salt thereof according to claim 1, wherein $R^1$ represents a t-butylcarbamoyl group, isopentylcarbamoyl group, cyclopentylcarbamoyl group, isopentylcarbonyl group, cyclopentylcarbonyl group, t-butoxycarbonyl group, benzoyl group or benzyloxycarbonyl group.

10. The compound and a salt thereof according to claim 1, wherein $R^2$ represents a phenyl group, 2-fluorophenyl group, 4-fluorophenyl group, 2-methylphenyl group, 3-methylphenyl group, 4-methylphenyl group, 2,4-dimethylphenyl group, 2,5-dimethylphenyl group or 2-(trifluoromethyl)phenyl group.

11. The compound and a salt thereof according to claim 1, wherein $R^3$ represents a benzyl ester group, amino group, methylamino group, isobutylamino group, 2-benzyloxyethylamino group, 2,4-dimethoxybenzylamino group, 2-(2-naphthylmethyl)oxyethylamino group, 2-(3-pyridylmethyl)oxyethylamino group, 2-benzhydryloxyethylamino group or morpholino group.

12. The compound and a salt thereof according to claim 1, wherein A represents a direct bond, methionine, methioninesulfone, arginine, aspartic acid, asparagine, glutamine, citrulline, ornithine, aspartic acid β-benzyl ester, $N^ω$-nitro-arginine, aspartic acid-glutamine or asparagine-glutamine.

13. The compound and a salt. thereof according to claim 1, wherein $R^1$ represents a t-butylcarbamoyl group, isopentylcarbamoyl group, cyclopentylcarbamoyl group, isopentylcarbonyl group, cyclopentylcarbonyl group, t-butoxycarbonyl group, benzoyl group or benzyloxycarbonyl group; $R^2$ represents a phenyl group, 2-fluorophenyl group, 4-fluorophenyl group, 2-methylphenyl group, 3-methylphenyl group, 4-methylphenyl group, 2,4-dimethylphenyl group, 2,5-dimethylphenyl group or 2-(trifluoromethyl)phenyl group; $R^3$ represents a benzyl ester group, amino group, methylamino group, isobutylamino group, 2-benzyloxyethylamino group, 2,4-dimethoxybenzylamino group, 2-(2-naphthylmethyl) oxyethylamino group, 2-(3-pyridylmethyl)oxyethylamino group, 2-benzhydryloxyethylamino group or morpholino group; and A represents a direct bond, methionine, methioninesulfone, arginine, aspartic acid, asparagine, glutamine, citrulline, ornithine, aspartic acid β-benzyl ester, $N^ω$-nitro-arginine, aspartic acid-glutamine or asparagine-glutamine.

14. The compound and a salt thereof according to claim 1, wherein the compound is selected from the group consisting of:

Boc-Asp(OBzl)-Gln-Trp-AzPhe-NH$_2$
Boc-Gln-Trp-AzPhe-NH(CH$_2$)$_2$OCH$_2$Ph
Boc-Asp (OBzl)-Gln-Trp-AzPhe-NH(CH$_2$)$_2$OCH$_2$Ph
i-Pent-CO-Gln-Trp-AzPhe-NH(CH$_2$)$_2$OCH$_2$Ph
Bz-Gln-Trp-AzPhe-NH(CH$_2$)$_2$OCH$_2$Ph
cyPent-CO-Gln-Trp-AzPhe-NH(CH$_2$)$_2$OCH$_2$Ph
t-Bu-NHCO-Gln-Trp-AzPhe-NH(CH$_2$)$_2$OCH$_2$Ph i-Pent-NHCO-Gln-Trp-AzPhe-NH(CH$_2$)$_2$OCH$_2$Ph
cyPent-NHCO-Gln-Trp-AzPhe-NH(CH$_2$)$_2$OCH$_2$Ph
Boc-Met (O$_2$)-Trp-AzPhe-NH(CH$_2$)$_2$OCH$_2$Ph
Boc-Asn-Trp-AzPhe-NH(CH$_2$)$_2$OCH$_2$Ph
Z-Asn-Trp-AzPhe-NH(CH$_2$)$_2$OCH$_2$Ph
Boc-Asp(OBzl)-Gln-Trp-AzPhe-OBzl
Boc-Gln-Trp-Azphe(4-F) -NH (CH$_2$)2OCH2Ph
t-Bu-NHCO-Gln-Trp-AzPhe(4-F)-NH(CH$_2$)$_2$OCH$_2$Ph
t-Bu-NHCO-Gln-Trp-AzPhe(2-Me)-NH(CH$_2$)$_2$OCH$_2$Ph
t-Bu-NHCO-Gln-Trp-AzPhe(3-Me)-NH(CH$_2$)$_2$OCH$_2$Ph
t-Bu-NHCO-Gln-Trp-AzPhe(4-Me)-NH(CH$_2$)$_2$OCH$_2$Ph
t-Bu-NHCO-Gln-Trp-AzPhe(2,4-diMe)-NH(CH$_2$)$_2$OCH$_2$Ph
t-Bu-NHCO-Gln-Trp-AzPhe(2,5-diMe)-NH(CH$_2$)$_2$OCH$_2$Ph
t-Bu-NHCO-Gln-Trp-AzPhe(2-F)-NH(CH$_2$)$_2$OCH$_2$Ph and
t-Bu-NHCO-Gln-Trp-AzPhe(2-CF$_3$)-NH(CH$_2$)$_2$OCH$_2$Ph
wherein Boc represents t-butoxycarbonyl, Asp represents aspartic acid, OBzl represents benzyl ester, Gln represents glutamine, Irp represents tryptophan, AzPhe represents α-aza-phenylalanine, Ph represents phenyl, i-Pent represents isopentyl, Bz represents benzoyl, cyPent represents cyclopentyl, t-Bu represents tertbutyl, Met(O$_2$) represents methioninesulfone, Asn represents asparagine, Z represents benzyloxycarbonyl, AzPhe(4-F) represents α-aza-4-fluorophenylalanine, AzPhe(2-Me) represents α-aza-2-methyl-phenylalanine, AzPhe(3-Me) represents α-aza-3-methyl-phenylalanine, AzPhe(4-Me) represents α-aza-4-methyl-phenylalanine, AzPhe(4-iPr) represents α-aza-4-isopropyl-phenylalanine, AzPhe(2,4-diMe) represents α-aza-2,4-dimethylphenylalanine, AzPhe(2,5-diMe) represents α-aza-2,5-dimethylphenylalanine, AzPhe(2-F) represents α-aza-2-fluoro-phenylalanine, and AzPhe(2-CF$_3$) represents α-aza-2-(trifluoromethyl)-phenylalanine.

15. An agent for curing nervous inflammation of respiratory apparatus, asthma and bronchospasm comprising the azapeptide compound represented by the formula (I) or a salt thereof according to claim 1 as an active ingredient, and a pharmaceutically acceptable carrier.

16. The agent according to claim 15, wherein the compound is administered in an amount of 0.01 to 100 mg per 1 kg of body weight of a mammal.

17. The agent according to claim 15, wherein the compound is administered in an amount of 0.1 to 50 mg per 1 kg of body weight of a mammal.

* * * * *